United States Patent
Yum et al.

(10) Patent No.: US 8,216,589 B2
(45) Date of Patent: Jul. 10, 2012

(54) HBV VACCINE AND A PROCESS OF PREPARING THE SAME

(75) Inventors: Jung Sun Yum, Gyeonggi-do (KR); Byung Cheol Ahn, Gyeonggi-do (KR); Hyun Jin Jo, Gyeonggi-do (KR); Dong Yeon Kim, Seoul (KR); Joo Youn Lee, Gyeonggi-do (KR); Ki Hyun Kim, Seoul (KR); Jae Seung Yoon, Gyeonggi-do (KR); Hong Mo Moon, Gyeonggi-do (KR)

(73) Assignee: Dobeel Corporation, Seongnam-si (KR)

( * ) Notice: Subject to any disclaimer, the term of this patent is extended or adjusted under 35 U.S.C. 154(b) by 830 days.

(21) Appl. No.: 12/225,341

(22) PCT Filed: Jan. 28, 2008

(86) PCT No.: PCT/KR2008/000518
§ 371 (c)(1),
(2), (4) Date: Sep. 19, 2008

(87) PCT Pub. No.: WO2008/093976
PCT Pub. Date: Aug. 7, 2008

(65) Prior Publication Data
US 2011/0165194 A1 Jul. 7, 2011

(30) Foreign Application Priority Data
Jan. 31, 2007 (KR) ........................ 10-2007-0010167

(51) Int. Cl.
*A61K 39/29* (2006.01)
*C12N 15/09* (2006.01)
*C12N 5/10* (2006.01)
*C12N 1/21* (2006.01)
*C12N 15/63* (2006.01)

(52) U.S. Cl. .................... 424/227.1; 435/69.3; 435/325; 435/358; 435/252.33; 435/320.1

(58) Field of Classification Search .................. None
See application file for complete search history.

(56) References Cited

U.S. PATENT DOCUMENTS

| | | | |
|---|---|---|---|
| 2002/0177124 A1* | 11/2002 | Coleman et al. | 435/5 |
| 2003/0190308 A1* | 10/2003 | Braun et al. | 424/93.2 |
| 2004/0106174 A1* | 6/2004 | Jones et al. | 435/69.1 |
| 2006/0166187 A1* | 7/2006 | Maki et al. | 435/5 |
| 2011/0165194 A1* | 7/2011 | Yum et al. | 424/227.1 |

OTHER PUBLICATIONS

Sequence alignment of instant SEQ ID 6 with Geneseq database ID AEI26795 from CN1690206 of Li et al., Nov. 2005.*
Zinckgraf et al. (Vaccine. 2003; 21: 1640-1649).*

* cited by examiner

*Primary Examiner* — Shanon A Foley
(74) *Attorney, Agent, or Firm* — Vorys, Sater, Seymour and Pease LLP; Mih Suhn Koh

(57) ABSTRACT

The present invention relates to an HBV vaccine comprising an entire hepatitis B surface antigen of L protein, M protein and S protein, in which the produced antigens form virus-like particles, and a multi-antigen vaccine further comprising an HBV core antigen in addition to the entire surface antigen, and a method for preparing the same. The vaccines provide various epitopes and have excellent immunogenicity to induce a strong humoral immune response as well as a cell-mediated immune response.

15 Claims, 24 Drawing Sheets

[Fig. 1]
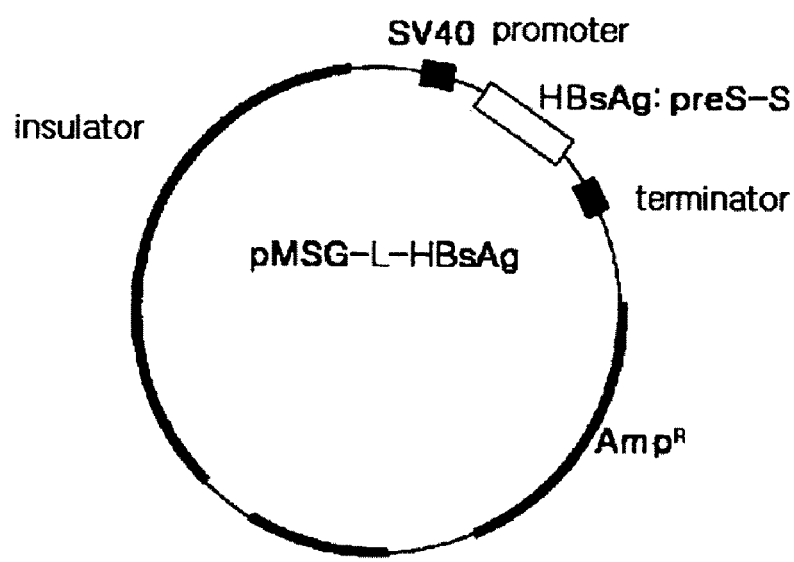

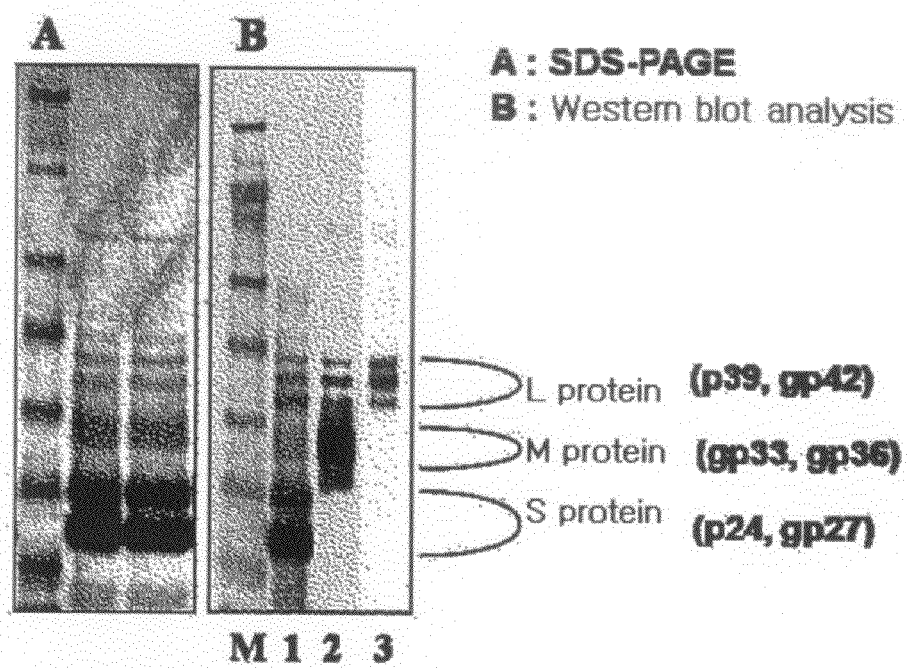

[Fig. 3]
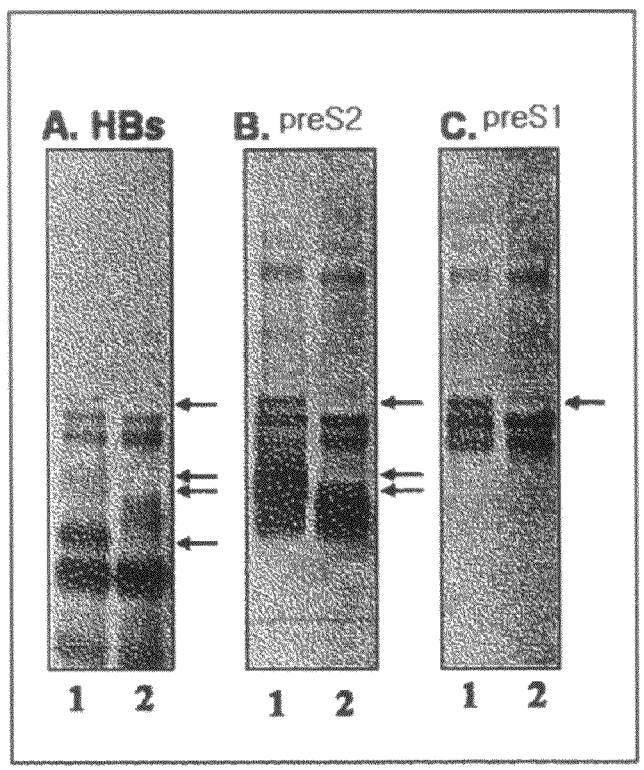
A. Western blot with anti-S antibody
B. Western blot with anti-preS2 antibody
C. Western blot with anti-preS1 antibody
Lane 1: Entire surface protein (before N-glycosidase F treatment)
Lane 2: Entire surface protein (after N-glycosidase F treatment)

[Fig. 4]
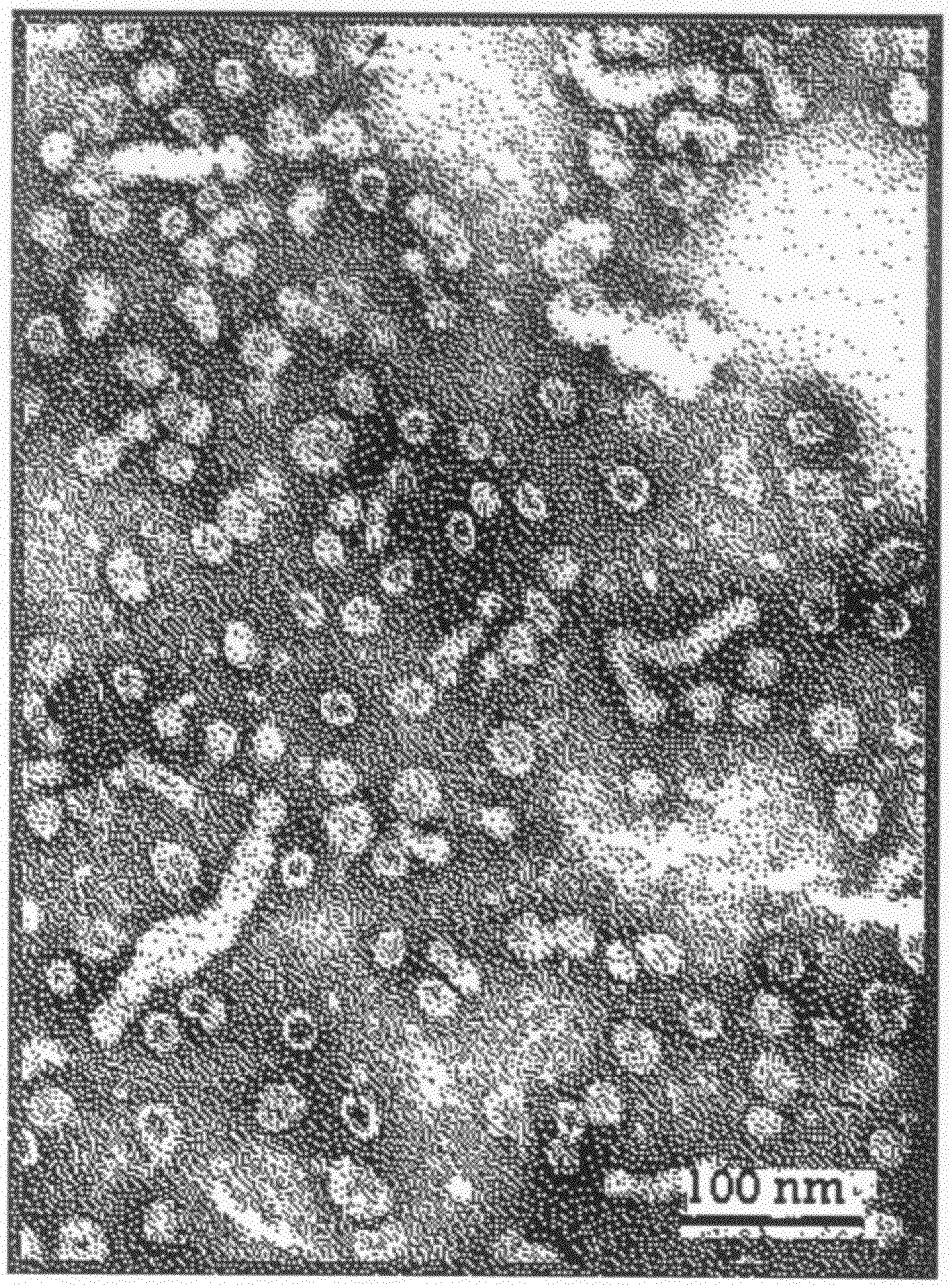

[Fig. 5]
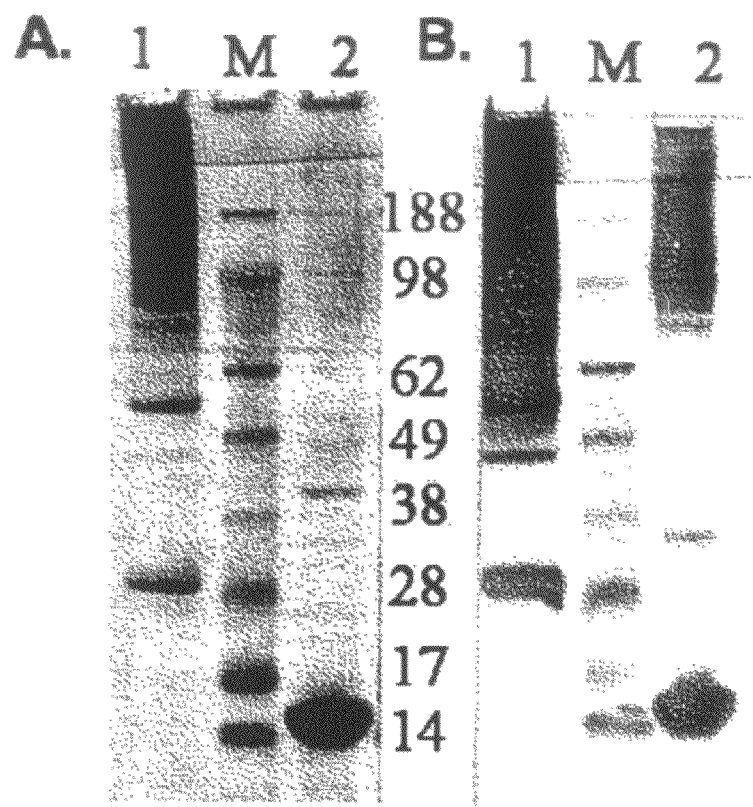
M. Marker
Lane 1. Non-reduced condition
Lane 2. Reduced condition

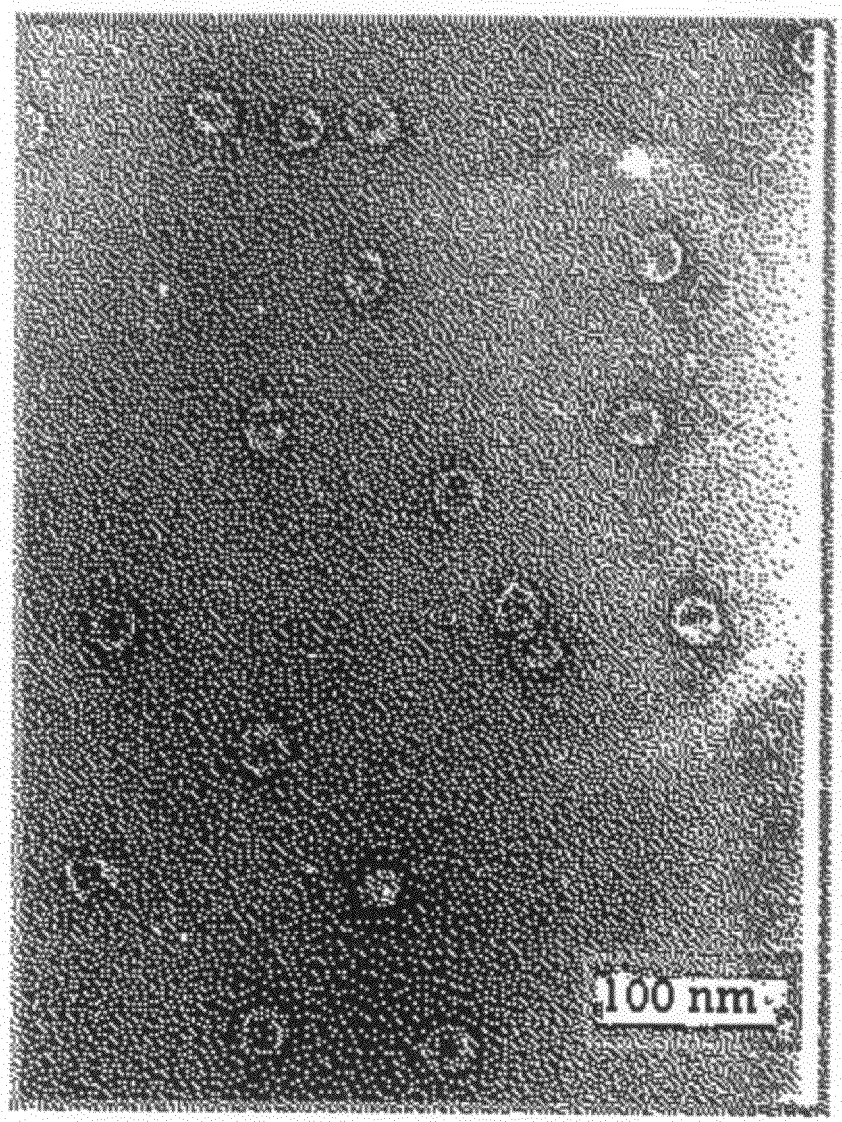
[Fig. 6]

[Fig. 7]
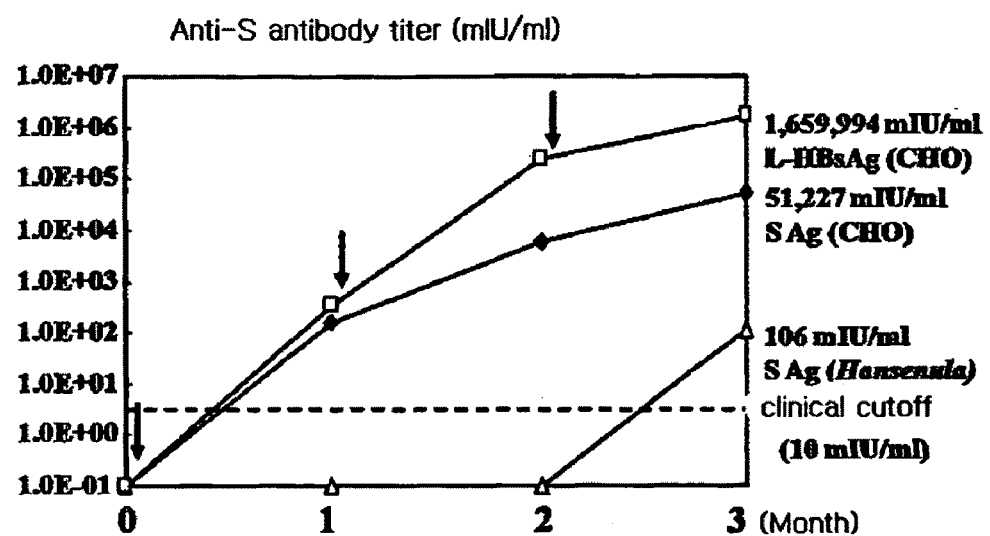

[Fig. 8]

| Group | Antigen (host) | Amount of antigen at ED50 |
|---|---|---|
| Group 1 | S Ag (Yeast) | 1.41 µg |
| Group 2 | S Ag (CHO) | 0.469 µg |
| Group 3 | L-HBsAg (CHO) | <0.156 µg |

[Fig. 9]
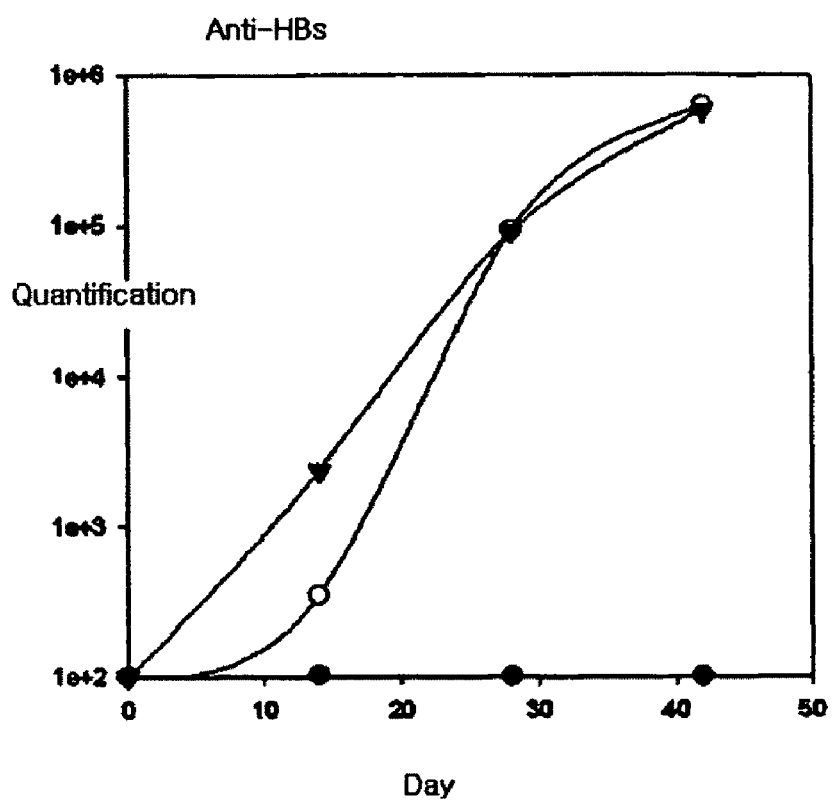

[Fig. 10]
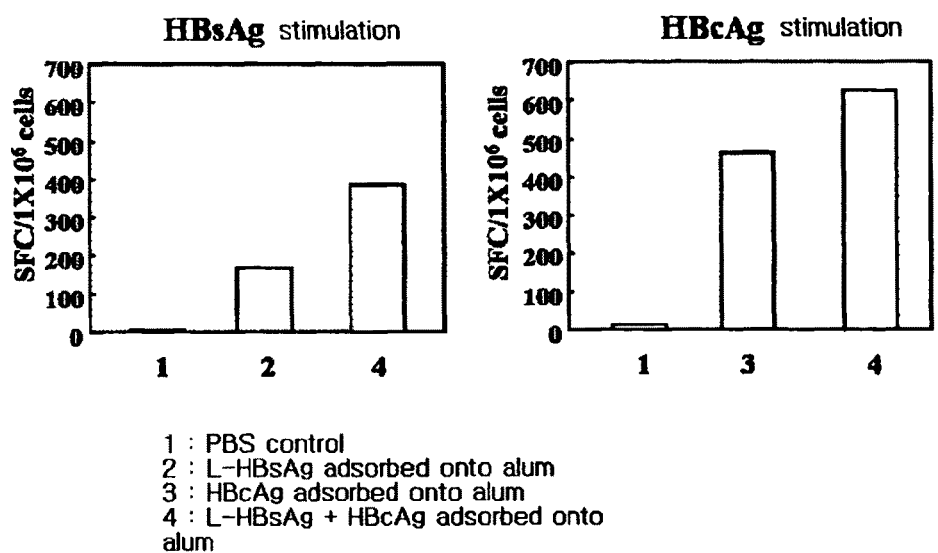
1 : PBS control
2 : L-HBsAg adsorbed onto alum
3 : HBcAg adsorbed onto alum
4 : L-HBsAg + HBcAg adsorbed onto alum

[Fig. 11]
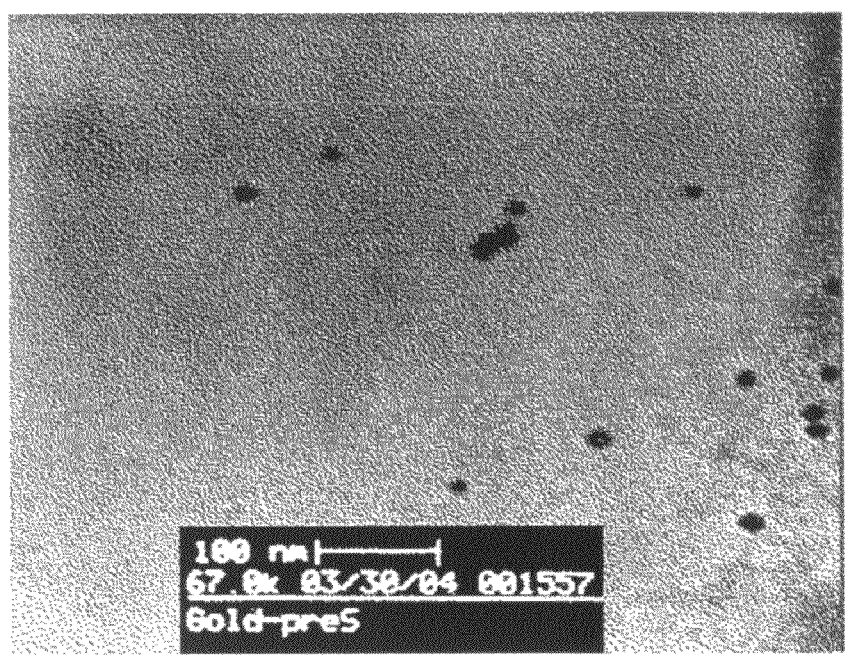

[Fig. 12]
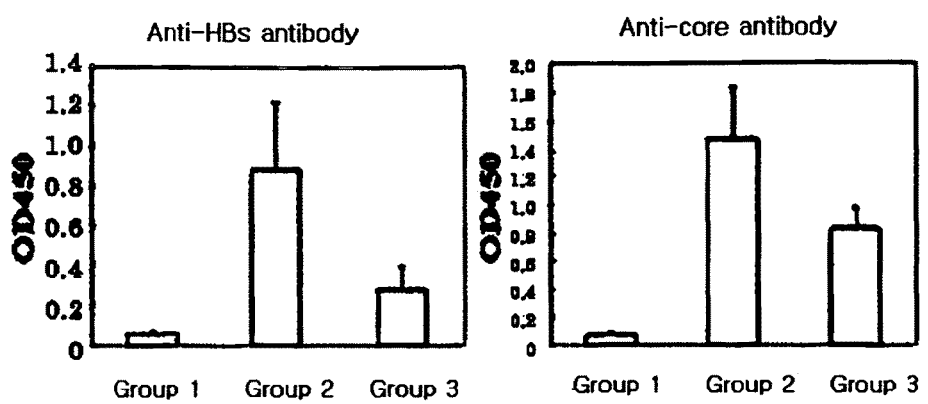

[Fig. 13]
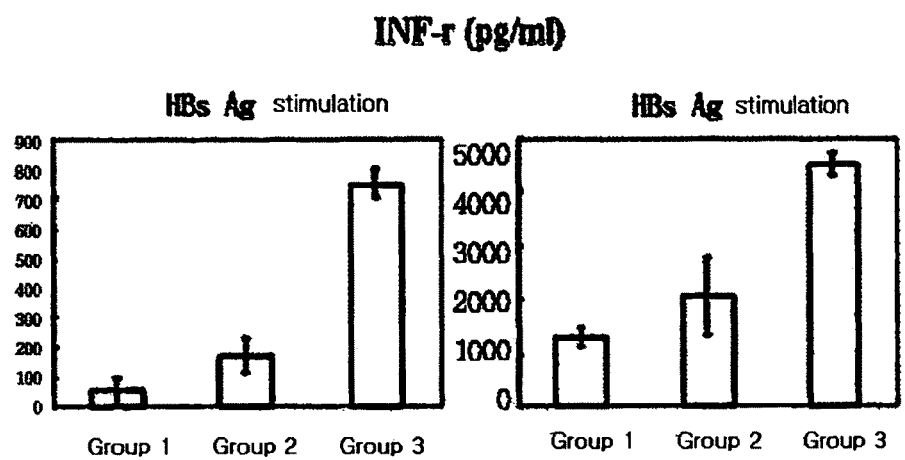

[Fig. 14]
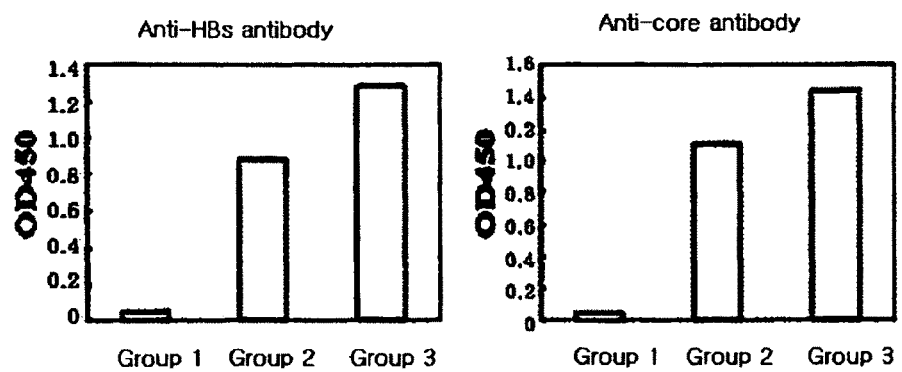

[Fig. 15]
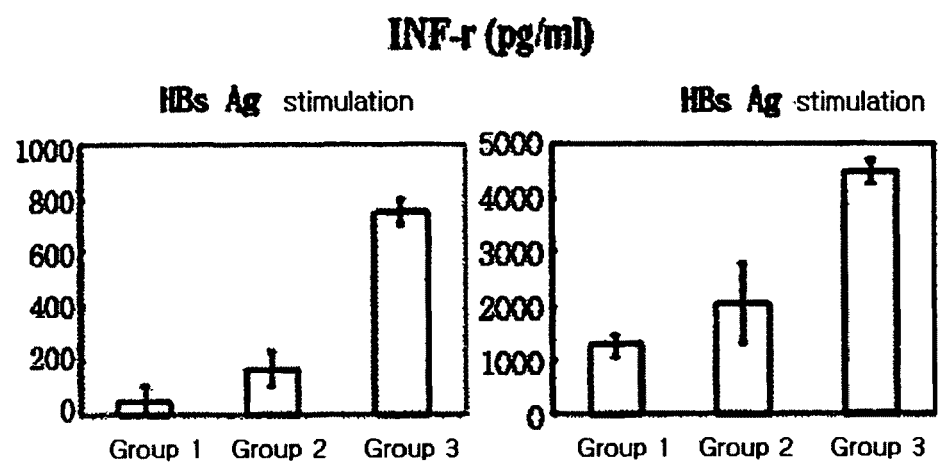

[Fig. 16]
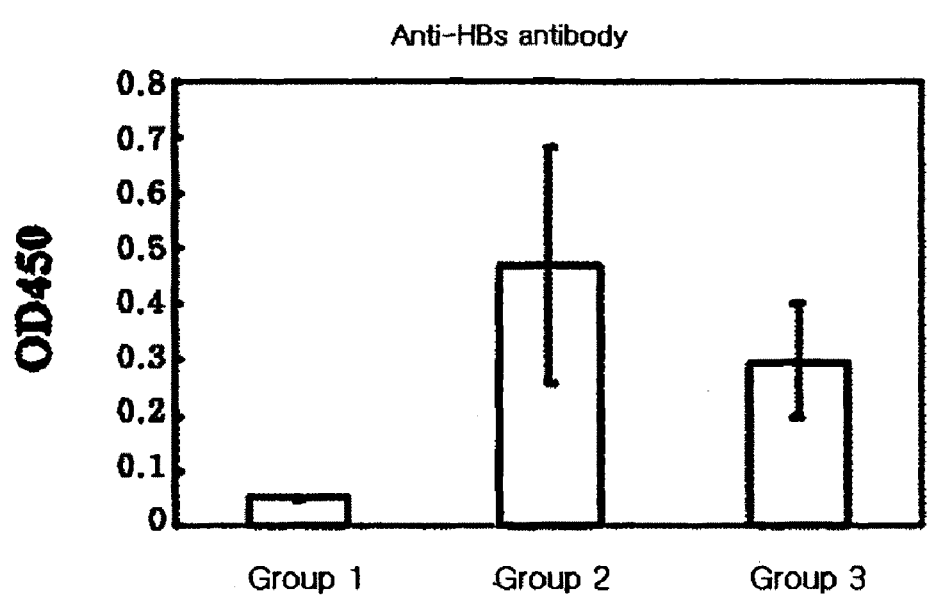

[Fig. 17]
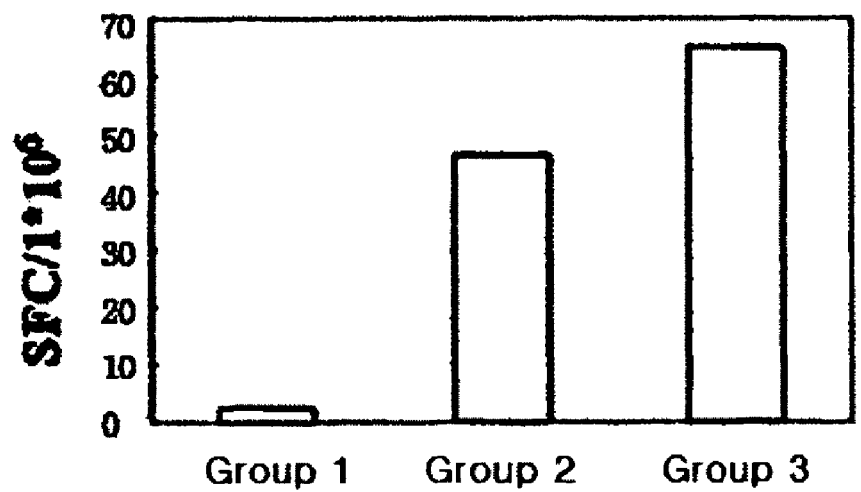

{Fig. 18}
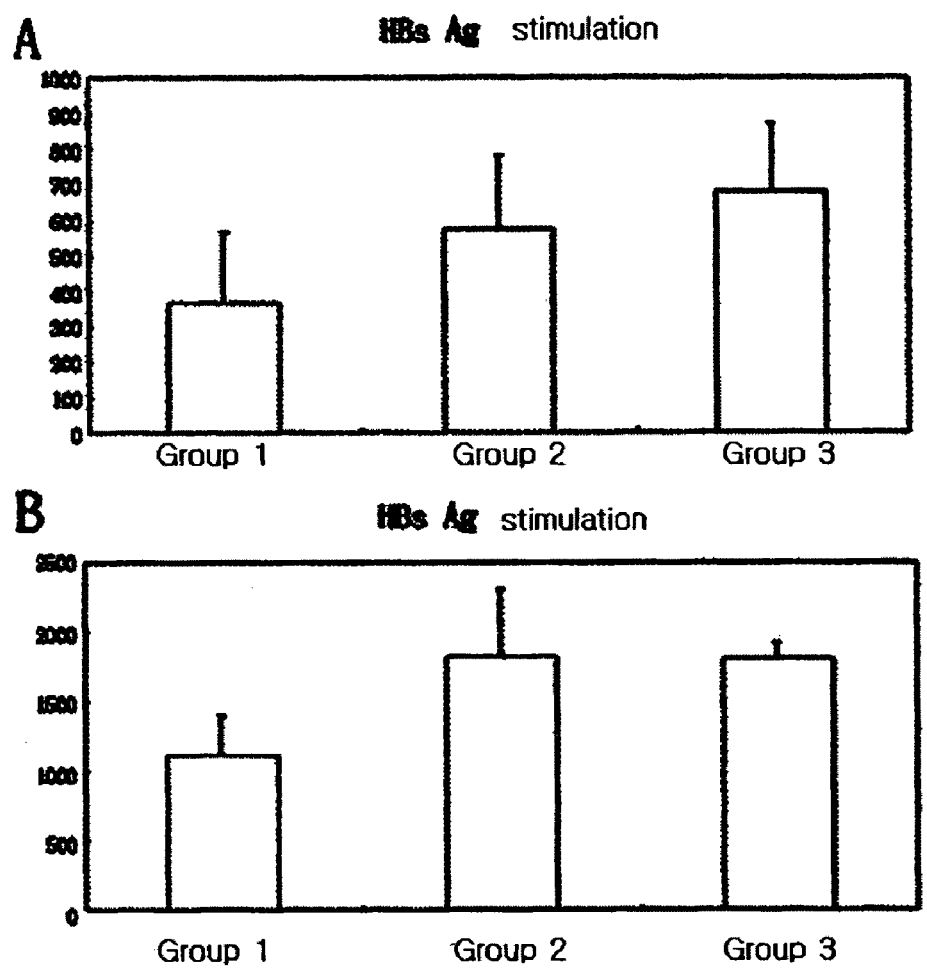

[Fig. 19]
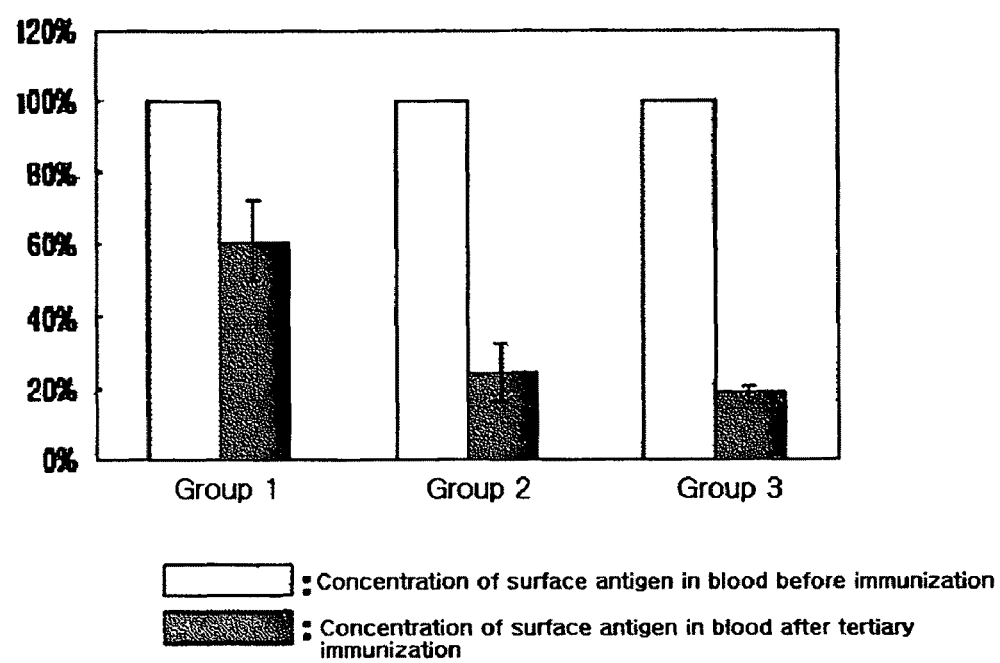

[Fig. 20]
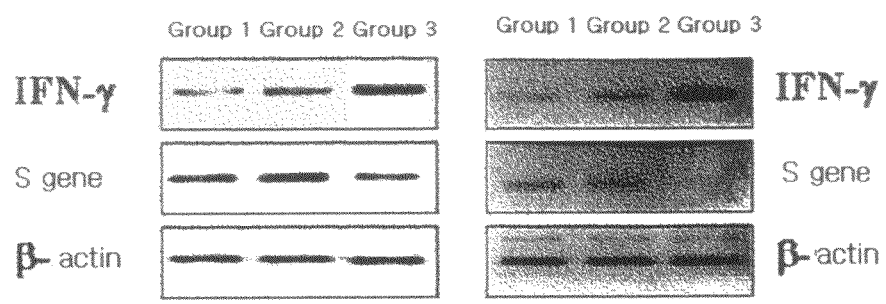

[Fig. 21]
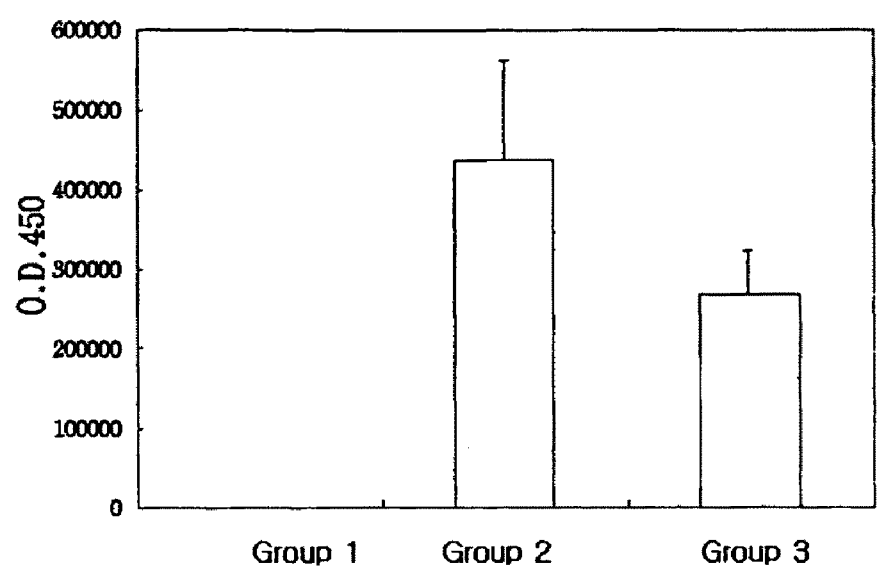

[Fig. 22]
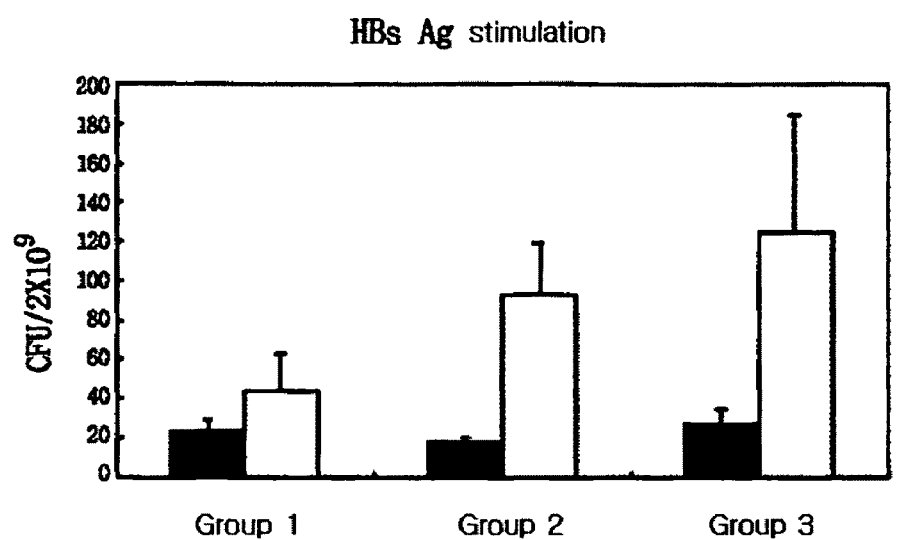

[Fig. 23]
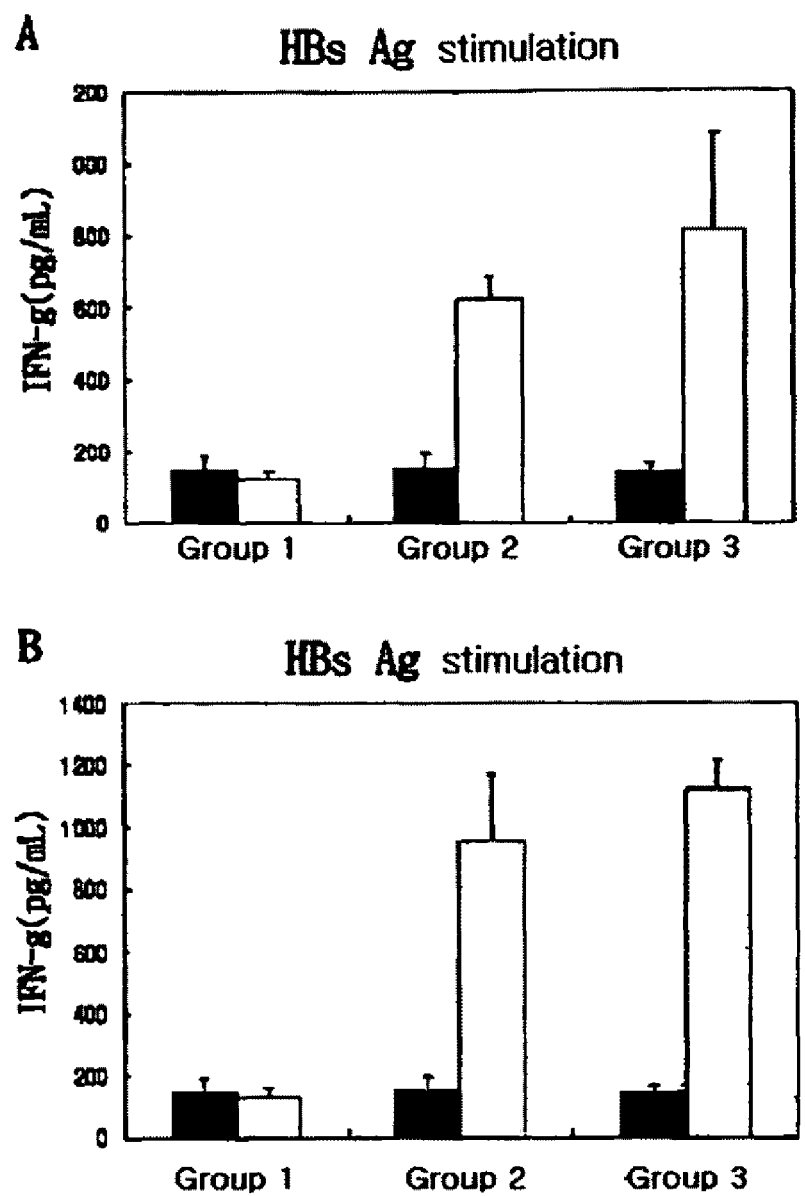

[Fig. 24]
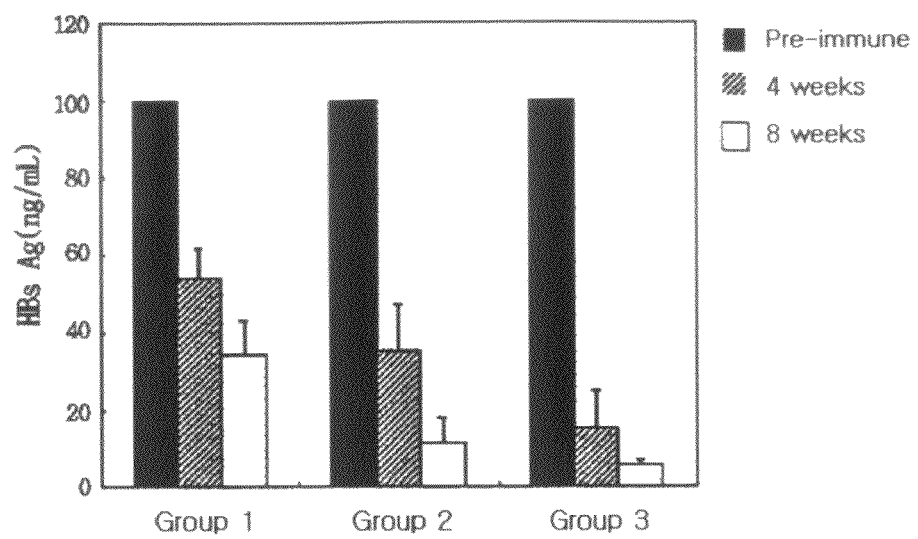

SEQUENCE LISTING

```
<160> NUMBER OF SEQ ID NOS: 14

<210> SEQ ID NO 1
<211> LENGTH: 2782
<212> TYPE: DNA
<213> ORGANISM: Hepatitis B virus
<220> FEATURE:
<223> OTHER INFORMATION: Envelope gene

<400> SEQUENCE: 1
agatctcaat ctcgggaatc tcaatgttag tatcccttgg actcataagg tgggaaactt        60
tactgggctt tattcttcta ctgtacctgt ctttaatcct gagtggcaaa ctccctcctt       120
```

```
tcctaacatt catttacagg aggacattat taatagatgt caacaatatg tgggccctct    180
tacagttaat gaaaaaagga gattaaaatt aattatgcct gctaggtttt atcctaacct    240
taccaaatat ttgcccttgg ataaaggcat taaaccttat tatcctgaac atgcagttaa    300
tcattacttc aaaactaggc attatttaca tactctgtgg aaggctggca ttctatataa    360
gagagaaact acacgcagcg cttcattttg tgggtcacca tattcttggg aacaagagct    420
acagcatggg aggttggtct tccaaacctc gacaaggcat ggggacgaat ctttctgttc    480
ccaatcctct gggattcttt cccgatcacc agttggaccc tgcgttcgga gccaactcaa    540
acaatccaga ttgggacttc aaccccaaca aggatcactg ccagaggca aatcaggtag    600 gagtgggagc attcgggcca gggttcaccc caccacacgg cggtcttttg gggtggagcc    660
ctcaggctca gggcatattg acaacagtgc cagcagcgcc tcctcctgcc tccaccaatc    720
ggcagtcagg aagacagcct actcccatct ctccacctct aagagacagt catcctcagg    780
ccatgcagtg gaactccacc acattccacc aagctctgct agatcccaga gtgaggggcc    840
tatattttcc tgctggtggc tccagttccg gaacagtaaa ccctgttccg actactgcct    900
cacccatatc gtcaatcttc tcgaggactg ggaccctgc accgaacatg gagagcacaa    960
catcaggatt cctaggaccc ctgctcgtgt tacaggcggg gttttctctg ttgacaagaa   1020
tcctcacaat accacagagt ctagactcgt ggtggacttc tctcaatttt ctaggggag   1080 cacccacgtg tcctggccaa aattcgcagt ccccaacctc caatcactca ccaacctctt   1140
gtcctccaat ttgtcctggc tatcgctgga tgtgtctgcg gcgttttatc atattcctct   1200
tcatcctgct gctatgcctc atcttcttgt tggttcttct ggactaccaa ggtatgttgc   1260
ccgtttgtcc tctacttcca ggaacatcaa ctaccagcac gggaccatgc aagacctgca   1320
cgattcctgc tcaaggaacc tctatgtttc cctcttgttg ctgtacaaaa ccttcggacg   1380
gaaactgcac ttgtattccc atcccatcat cctgggcttt cgcaagattc ctatgggagt   1440
gggcctcagt ccgtttctcc tggctcagtt tactagtgcc atttgttcag tggttcgcag   1500
ggctttcccc cactgtttgg ctttcagtta tatggatgat gtggtattgg gggccaagtc   1560
tgtacaacat cttgagtccc tttttacctc tattaccaat tttcttctgt ctttgggtat   1620
acatttaaac cctaataaaa ccaagcgttg gggctactcc cttaacttca tgggatatgt   1680
aattggaagc tggggtactt taccacagga acatattgta ctaaagctca aggaatgttt   1740
tcggaaactg cctgtaaata gacctattga ttggaaagta tgtcaaagaa ttgtgggtct   1800
tttgggcttt gctgccccctt ttacacaatg tggctatcct gccttgatgc ctttatatgc   1860
atgtatacaa gctaagcagg ctttcacttt ttcgccaact tacaaggcct ttctgtgtaa   1920
acaatatctg caccttttacc ccgttgcccg gcaacggtca ggtctctgcc aagtgtttgc   1980
tgacgcaacc cccactggat ggggcttggc cataggccat cggcgcatgc gtggaacctt   2040
tgtggctcct ctgccgatcc atactgcgga actcctagca gcgtgttttg ctcgcagcag   2100
gtctggagca acacttatcg ggactgacaa ctctgttgtc ctctctcgga aatacacctc   2160
cttcccatgg ctgctcggat gtgctgccaa ctggatcctg cgcgggacgt cctttgtcta   2220
cgtcccgtcg gcgctgaatc ccgcggacga cccgtctcgg ggccgtttgg gcctctaccg   2280
tccccttctt catctgccgt tccggccgac cacggggcgc acctctcttt acgcggtctc   2340
cccgtctgtg ccttctcatc taccggaccg tgtgcacttc gcttcacctc tgcacgtcgc   2400
atggagacca ccgtgaacgc ccaccaggtc ttgcccaagg tcttacataa gaggactctt   2460
ggactctcag caatgtcaac gaccgacctt gaggcatact tcaaagactg tttgtttaaa   2520
```

-continued

```
gactgggagg agttgggga ggagattagg ttaaaggtct ttgtactagg aggctgtagg    2580
cataaattgg tctgtgcacc agcaccatgc aactttttca cctctgccta atcatctcat    2640
gttcatgtcc tactgttcaa gcctccaagc tgtgccttgg gtggctttgg ggcatggaca    2700
ttgacccgta taaagaattt ggagcttctg tggagttact ctcttttttg ccttctgact    2760
tctttccttc tattcgagat ct                                            2782
```

```
<210> SEQ ID NO 2
<211> LENGTH: 21
<212> TYPE: DNA
<213> ORGANISM: Artificial Sequence
<220> FEATURE:
<223> OTHER INFORMATION: Forward primer for PCR

<400> SEQUENCE: 2
ggaagatctc aatctcggga a                                              21

<210> SEQ ID NO 3
<211> LENGTH: 24
<212> TYPE: DNA
<213> ORGANISM: Artificial Sequence
<220> FEATURE:
<223> OTHER INFORMATION: Reverse primer for PCR

<400> SEQUENCE: 3
ggaagatctc gaatagaagg aaag                                           24

<210> SEQ ID NO 4
<211> LENGTH: 400
<212> TYPE: PRT
<213> ORGANISM: Hepatitis B virus
<220> FEATURE:
<223> OTHER INFORMATION: L-HBsAg

<400> SEQUENCE: 4
```

Met Gly Gly Trp Ser Ser Lys Pro Arg Gln Gly Met Gly Thr Asn Leu
 1               5                  10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

```
Phe Phe Leu Leu Thr Arg Ile Leu Thr Ile Pro Gln Ser Leu Asp Ser
            195                 200                 205

Trp Trp Thr Ser Leu Asn Phe Leu Gly Gly Ala Pro Thr Cys Pro Gly
        210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
                260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ile Pro Ala Gln Gly
        290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
        340                 345                 350

Phe Val Gln Trp Phe Ala Gly Leu Ser Pro Thr Val Trp Leu Ser Val
        355                 360                 365

Ile Trp Met Met Trp Tyr Trp Gly Pro Ser Leu Tyr Asn Ile Leu Ser
        370                 375                 380

Pro Phe Leu Pro Leu Leu Pro Ile Phe Phe Cys Leu Trp Val Tyr Ile
385                 390                 395                 400

<210> SEQ ID NO 5
<211> LENGTH: 149
<212> TYPE: PRT
<213> ORGANISM: Hepatitis B virus
<220> FEATURE:
<223> OTHER INFORMATION: HBV Core antigen except the arginine
      cluster at C-terminal

<400> SEQUENCE: 5

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val
145
```

```
<210> SEQ ID NO 6
<211> LENGTH: 447
<212> TYPE: DNA
<213> ORGANISM: Hepatitis B virus
<220> FEATURE:
<223> OTHER INFORMATION: HBV Core antigen except the arginine cluster
      at C-terminal

<400> SEQUENCE: 6
atggacattg acccgtataa agaatttgga gcttctgtgg agttactctc ttttttgcct      60
tctgacttct ttccttctat tcgagatctc ctcgacaccg cctctgctct gtatcgggag     120
gccttagagt ctccggaaca ttgttcacct caccatacag cactcaggca agctattctg     180
tgttggggtg agttgatgaa tctggccacc tgggtgggaa gtaatttgga agacccagca     240
tccagggaat tagtagtcag ctatgtcaac gttaatatgg cctaaaaat cagacaacta     300 ttgtggtttc acatttcctg tcttactttt ggaagagaaa ctgttcttga gtatttggtg     360
tcttttggag tgtggattcg cactcctccc gcttacagac caccaaatgc ccctatctta     420
tcaacacttc cggaaactac tgttgtt                                          447

<210> SEQ ID NO 7
<211> LENGTH: 23
<212> TYPE: DNA
<213> ORGANISM: Artificial Sequence
<220> FEATURE:
<223> OTHER INFORMATION: Forward primer for PCR

<400> SEQUENCE: 7
ccccatatgg acattgaccc gta                                               23

<210> SEQ ID NO 8
<211> LENGTH: 27
<212> TYPE: DNA
<213> ORGANISM: Artificial Sequence
<220> FEATURE:
<223> OTHER INFORMATION: Reverse primer for PCR

<400> SEQUENCE: 8
cgcggatcca acaacagtag tttccgg                                           27

<210> SEQ ID NO 9
<211> LENGTH: 20
<212> TYPE: DNA
<213> ORGANISM: Artificial Sequence
<220> FEATURE:
<223> OTHER INFORMATION: Forward primer for RT-PCR

<400> SEQUENCE: 9
atggagagca caacatcagg                                                   20

<210> SEQ ID NO 10
<211> LENGTH: 18
<212> TYPE: DNA
<213> ORGANISM: Artificial Sequence
<220> FEATURE:
<223> OTHER INFORMATION: Reverse primer for RT-PCR

<400> SEQUENCE: 10
ttaaatgtat accctaag                                                     18

<210> SEQ ID NO 11
<211> LENGTH: 26
<212> TYPE: DNA
```

```
<213> ORGANISM: Artificial Sequence
<220> FEATURE:
<223> OTHER INFORMATION: Forward primer for RT-PCR

<400> SEQUENCE: 11
agcggctgac tgaactcaga ttgtag                                          26

<210> SEQ ID NO 12
<211> LENGTH: 24
<212> TYPE: DNA
<213> ORGANISM: Artificial Sequence
<220> FEATURE:
<223> OTHER INFORMATION: Reverse primer for RT-PCR

<400> SEQUENCE: 12
gtcacagttt tcagctgtat aggg                                            24

<210> SEQ ID NO 13
<211> LENGTH: 20
<212> TYPE: DNA
<213> ORGANISM: Artificial Sequence
<220> FEATURE:
<223> OTHER INFORMATION: Forward primer for RT-PCR

<400> SEQUENCE: 13
tcctgtggca tccatgaaac                                                 20

<210> SEQ ID NO 14
<211> LENGTH: 19
<212> TYPE: DNA
<213> ORGANISM: Artificial Sequence
<220> FEATURE:
<223> OTHER INFORMATION: Reverse primer for RT-PCR

<400> SEQUENCE: 14
cttcgtgaac gccacgtgc                                                  19
```

HBV VACCINE AND A PROCESS OF PREPARING THE SAME

CROSS REFERENCE TO RELATED APPLICATION

This application is based on and claims the benefit of, PCT/KR2008/000518 filed 28 Jan. 2008 and Korean patent application serial no.: 10-20070010167 filed Jan. 31, 2007 now Korean patent no.: 10-0836745 issued Jun. 3, 2008.

The official copy of the sequence listing is submitted electronically via EFS-WEB as an ASCII formatted sequence listing with a file name "12225341_Sequence_Listing.txt", created on Mar. 22, 2011, and having a size of 11 kilobytes, and it was filed concurrently with the specification. The sequence listing contained in this ASCII formatted document is part of the specification and is herein incorporated by reference in its entirety.

TECHNICAL FIELD

The present invention relates to a hepatitis B virus (HBV) vaccine comprising entire HBV surface antigen consisting of preS antigen and S antigen, a multi-HBV antigen vaccine further comprising an HBV core antigen in addition to the entire surface antigen, and a method for preparing the same.

BACKGROUND OF INVENTION

HBV infection causes acute hepatitis and chronic hepatitis. The majority of individuals who have HBV infection fully recover from the virus infection after 1 to 2 month, but about 10% of them become chronic hepatitis patients. Depending on the age of infection, the rate of becoming chronic infection is much worse, showing over 95% for newborns under the age of 2 months, decreasing as aging progresses, and becoming about 25% for children of age five. Chronic infection of HBV causes increased risk for the development of liver cirrhosis and cancer. HBV surface antigen (HBsAg) is detected in the blood from patients with chronic infection of HBV, however, anti-HBsAg antibody does not appear due to immune tolerance development. Therefore, the final goal for the treatment of chronic HBV infection is to induce anti-HBsAg antibody in serum and remove HBV from the blood and liver.

The therapeutic vaccine described in the present invention is suitable for the treatment of HBV chronic infection, because it breaks immune tolerance and induces immune response against HBV to remove HBV antigen from the blood. Therapeutic vaccines against chronic HBV infection should meet the following requirements; it must be able to break immune tolerance and induce immune responses against HBV, eliciting strong humoral and cell-mediated immunity to resolve the chronic viral infection.

After HBV infection, when polyclonal immune responses were induced, the infection would be resolved. Whereas, when weak oligoclonal immune responses were induced, the infection would lead to chronic infection. This finding suggests that a therapeutic vaccine must contain antigens capable of providing various epitopes needed to induce polyclonal immune responses.

The envelop antigen gene of HBV consists of preS (preS1 and preS2) and S region, and after transcription, three envelop proteins (L protein, M protein and S protein) are synthesized by alternate translation at each of the three initiation codons. L protein consists of about 400 amino acids depending on HBV subtype, comprising the preS1 domain, preS2 domain, and S domain, of which translation initiation starts at preS1 AUG codon. M protein consists of about 281 amino acids, comprising the preS2 domain and S domain, of which translation initiation starts at preS2. S protein consists of about 226 amino acids, comprising only the S domain, and makes up the most abundant portion in the virus particles. The S domains of these envelop proteins are embedded in lipid membrane and form rod-shaped 22 nm and 42 nm particles depending on the ratio of the three different sized envelop proteins. The preS1 and preS2 domains contained in M and L proteins are highly immunogenic and helps to induce S protein specific antibodies in certain congenic mice strains in which the S protein alone is not immunogenic.

As described above, providing the complete set of envelope antigen specific epitopes and HBV antigen as highly immunogenic particle forms is important, developing an HBV vaccine containing entire preS protein and S protein is the aim of present invention. In particular, both animal and human experiments have shown that the vaccine containing both preS and S antigens can induce stronger immune responses and much faster responses than vaccine containing only S antigen. That is, vaccine containing both of preS and S antigens is more immunogenic and induces faster immune responses, as compared to the vaccine containing only S antigen, thereby showing that the L protein is more useful as a therapeutic vaccine for the treatment of chronic hepatitis B.

However, most of commercially available HBV vaccines contain only S protein. This could be due to the fact that expression of the L-protein in particle form seen in HBV chronic patients has not been successful from eukaryotic cell expression systems such as *Saccharomyces cerevisiae* or *Hansenula polymorpha*.

Further, there have been attempts to coexpress a portion of preS antigen (in particular, preS2) and the S antigen in eukaryotic cells such as *Saccharomyces cerevisiae* or *Hansenula polymorpha*, however, the products were not found to have sufficient immunogenicity.

In addition, there were other attempts of producing HBV antigen, in which the preS gene was separately expressed to produce the preS antigen only, and then mixed with S antigen. However, the produced linear soluble form of preS antigens was not very immunogenic. Thus, the attempt of improving immunogenicity was unsuccessful in comparison to the entire surface antigen, in which the preS antigen and S antigen are coexpressed in the forms of particles wherein the preS antigens are located at the external surface of particles.

Accordingly, to improve immunogenicity, the preS and S antigens have to be simultaneously expressed, and the preS antigens have to be located on the external surface of particles consisting of S antigens. Recently, Savient Pharma in Israel developed an HBV vaccine, which they claim contains the entire surface antigen, that is, both the preS and S antigens.

The present inventors have successfully developed a CHO cell line that can produce HBV envelop antigen containing preS and S antigens in particle form. They found that, when the entire envelop gene of hepatitis B virus was introduced into a specific vector, all three types of surface proteins (L protein, M protein and S protein) were expressed in the form of particles seen in the blood of HBV chronic patients. Using this antigen, an HBV vaccine comprising the recombinant entire surface antigen has been developed that is highly effective in inducing strong immune responses in transgenic mice and produces HBV antigen in the blood but without any detectable amount of HBV specific antibody.

SUMMARY OF THE INVENTION

It is an object of the present invention to provide an HBV vaccine comprising the entire surface antigen consisting of three types of surface proteins (L protein, M protein and S protein) in particle form.

Preferably, it is an object of the present invention to provide the vaccine comprising an entire HBV surface antigen, in which L protein, M protein and S protein are coexpressed from one expression vector comprising the entire envelop gene encoding the preS1, preS2 and S antigens of hepatitis B virus, and wherein the produced preS antigens are located on the external surface of particles formed by these antigens.

It is another object of the present invention to provide a method for preparing a powerful HBV vaccine.

It is still another object of the present invention to provide a recombinant expression vector capable of expressing all of three types of surface protein (L protein, M protein, and S protein).

It is still another object of the present invention to provide a cell transformed with the recombinant expression vector.

It is still another object of the present invention to provide an immune therapy suitable for treating chronic HBV infection as a form of HBV vaccine.

It is still another object of the present invention to provide a multi-HBV antigen vaccine to enhance both humoral and cell-mediated immunity wherein the vaccine is prepared by adding a recombinant HBV core antigen and/or adjuvant to the vaccine.

BRIEF DESCRIPTION OF THE DRAWINGS

FIG. 1 is a schematic diagram of a vector expressing a recombinant entire surface antigen (S protein, M protein, L protein);

FIG. 2 is a photograph of SDS-PAGE and Western blot of the purified recombinant entire surface antigen (S protein, M protein, L protein);

FIG. 3 is a photograph of Western blot of the purified recombinant entire surface antigen treated with N-glycosidase;

FIG. 4 is an electron-microscopic photograph of the purified recombinant entire surface antigen;

FIG. 5 is a photograph of SDS-PAGE and Western blot of the purified recombinant core antigen (core Ag);

FIG. 6 is an electron-microscopic photograph of the purified recombinant core antigen;

FIG. 7 shows the comparison of antibody titers between the HBV vaccine comprising the entire surface antigen according to the present invention and known vaccines;

FIG. 8 shows the comparison of $ED_{50}$ between the HBV vaccine comprising the entire surface antigen according to the present invention and known vaccines;

FIG. 9 shows the induction of humoral immune response in normal mouse by the multi-antigen vaccine according to the present invention;

FIG. 10 shows the induction of cell-mediated immune response in normal mouse by the multi-antigen vaccine according to the present invention;

FIG. 11 is an electron-microscopic photograph of colloidal gold conjugate coated with preS;

FIG. 12 shows the induction of humoral immune response in normal mouse by colloidal gold conjugate;

FIG. 13 shows the induction of cell-mediated immune response in normal mouse by colloidal gold conjugate;

FIG. 14 shows the induction of a humoral immune response in a normal mouse by the therapeutic vaccine according to the present invention;

FIG. 15 shows the induction of a cell-mediated immune response in a normal mouse by the therapeutic vaccine according to the present invention;

FIG. 16 shows the induction of a humoral immune response in a transgenic mouse by the therapeutic vaccine according to the present invention;

FIG. 17 is the result of ELISPOT assay showing the induction of a cell-mediated immune response in a transgenic mouse by the therapeutic vaccine according to the present invention;

FIG. 18 is the result of ELISA assay showing the induction of a cell-mediated immune response in a transgenic mouse by the therapeutic vaccine according to the present invention;

FIG. 19 shows the reduction of surface antigen (virus-like particle) in blood by the therapeutic vaccine;

FIG. 20 shows the reduction of viral gene expression and increase of γ-interferon expression by the therapeutic vaccine;

FIG. 21 shows the induction of a humoral immune response in a transgenic mouse by the therapeutic vaccine according to the present invention;

FIG. 22 is the result of ELISPOT assay showing the induction of a cell-mediated immune response in a transgenic mouse by the therapeutic vaccine according to the present invention;

FIG. 23 is the result of ELISA assay showing the induction of a cell-mediated immune response in a transgenic mouse by the therapeutic vaccine according to the present invention; and FIG. 24 shows the reduction of surface antigen (virus-like particle) in blood by the therapeutic vaccine according to the present invention.

DETAILED DESCRIPTION OF THE INVENTION

In one embodiment, the present invention provides an HBV vaccine, comprising a recombinant entire surface antigen consisting of L protein, M protein and S protein in particle forms.

Hepatitis B virus surface antigen (HBsAg) is composed of three related envelope proteins which are synthesized by the alternate use of three translational start codons and a common stop codon. The HBsAg protein includes a major polypeptide of 226 amino acids, designated as S protein in a non-glycosylated (p24) and glycosylated (gp27) form. The middle-sized protein, M protein has an additional 55 amino acids at the N terminal region of S domain, which is termed the preS2 domain corresponding to gp33 and gp36. The largest L protein has an additional 119 amino acids (preS1 domain) at the N terminal region of M protein consisting of the S and preS2 domains, which is designated as p39 and gp42 according to glycosylation. In the native envelope HBsAg particles, the S domains of the L protein, M protein and S protein are covalently linked to one another by intermolecular disulfide bonds to form viral particles.

The relative significance of the immune response to each of the S, preS2, and preS1 domains are only partially understood, however, the immune response to preS antigen is reported to enhance immunogenicity of S antigen (Milich D. R. et al. Science 228:1195-1199, 1985; Milich D. R. et al. J Immunol 23:511-523, 1986; Milich D. R. et al. Proc Natl. Acad Sci USA 85:1610-1614, 1988). Further, it is reported that antibodies against preS antigens block attachment, endocytosis, and possibly membrane penetration of hepatitis B virus into hepatocytes (Neurath A. R et al. Nature 315:154-156, 1985; Neurath A. R et al. Vaccine 4:35-37, 1986; Gerlich W. H. et al. Vaccine 8:S63-S68, 1990). Accordingly, third-generation HBV vaccines containing both preS and S antigens can more effectively induce immune responses than vaccines containing the S antigen alone.

According to the present invention, an HBV vaccine comprising a recombinant HBV entire surface antigen can be prepared, in which the recombinant HBV entire surface antigen containing S, M and L proteins is expressed from one expression vector and preS antigens consisting of preS1 and preS2 are located on the external surface of particles which are formed by bonds between S antigens. The vaccine comprising the antigen of the present invention is useful as a therapeutic vaccine, since it induces a much stronger immune responses as compared to vaccines containing only S antigen or vaccines containing the separately expressed S and preS antigens in a mixed form.

Among known HBV vaccines, second-generation HBV vaccines contain only the S antigen, and third-generation HBV vaccines do not contain all of three surface antigens, but contain a portion of preS antigen and S antigen or contain hardly detectable amounts of preS antigen, even though they supposedly contain both preS and S antigens. This could be due to the loss of the pre S portion in the process of purification. Therefore, the produced surface antigen may not be as immunogenic as an entire surface antigen, or when the preS antigen and S antigen are separately expressed and presented in a mixed form. Thus, the surface antigens produced in the known HBV vaccines may not be as immunogenic as the entire surface antigen, in which preS antigens are coexpressed with S antigens and located on the external surface of particles formed by bonds between S antigens.

As described above, the present invention provides a recombinant HBV vaccine comprising the entire surface antigen, in which the three types of HBV surface proteins are coexpressed and form virus-like particles, including 22 nm and 42 nm rod-shaped particles.

The term "entire surface antigen (L-HBsAg)" or "entire recombinant HBV surface antigen" as used herein refers to antigen including all of the coexpressed three types of HBV surface proteins (S, M and L proteins), in which the preS antigens consisting of preS1 and preS2 are located on the external surface of particles formed by bonds between S antigens.

In preferred embodiment, the present invention provides an HBV vaccine further comprising an HBV core antigen, in addition to the entire HBV surface antigen.

The HBV core antigen is characterized in that it forms a virus-like particle, exhibits high immunogenicity, and induces strong cell-mediated immunity. Thus, it is expected that vaccines further comprising the core antigen in addition to the entire HBV surface antigen will induce strong immune responses, thereby being useful as a therapeutic vaccine, which is confirmed in Example 3. That is, it was found that the vaccine comprising both entire HBV surface antigen and core antigen more effectively induces cell-mediated immune responses than the vaccine comprising the entire HBV surface antigen alone. Thus, the vaccine comprising both entire HBV surface antigen and core antigen was found to be more useful as a therapeutic vaccine.

As described later in detail, the vaccine further comprising the HBV core antigen may be prepared by mixing the HBV core antigen with the entire HBV surface antigen prepared according to the method of the present invention. In the embodiments of the present invention, the HBV vaccine comprising only the entire HBV surface antigen according to the present invention is defined as a single antigen vaccine, and the HBV vaccine comprising both of the entire HBV surface antigen and core antigen according to the present invention is defined as a multi-antigen vaccine.

In still another embodiment, the present invention provides a recombinant expression vector that can efficiently co-express all of surface proteins, which constitutes HBV envelop proteins as seen in the blood of chronically infected HBV patients.

As described above, the most powerful HBV vaccine of the present invention can be prepared by coexpressing the three types of surface protein from one expression vector, in which the recombinant expression vector comprises the HBV envelope gene, that is, an entire polynucleotide encoding pre-S1, pre-S2 and S regions. Preferably, the base sequence may be provided in the form of entire HBV envelope gene, and more preferably HBV envelope gene represented by SEQ ID NO. 1

Further, for the preparation of the recombinant expression vector according to the present invention, a pMSG vector (KCCM10202), disclosed in Korean Patent Application No. 10-2000-0043996 and PCT/KR01/01285, may be preferably used. The pMSG vector contains a beta-globin MAR complementary sequence; a promoter of SV40 virus; and a transcription terminator having a specific base sequence, and is a vector capable of effectively expressing foreign genes in animal cells. The expression vector can successfully produce recombinant proteins in various animal cells, and produce a recombinant protein having the same structure and function compared to wild type protein. The pMSG vector is described in detail in Korean Patent Application No. 10-2000-0043996, and the disclosure thereof is incorporated herein by reference in its entirety.

In a specific embodiment of the present invention, the entire envelope gene encoding the entire HBV surface antigen was inserted into the pMSG vector to confirm whether all of L, M and S proteins were expressed or not (see FIG. 2). Further, it was found that the recombinant L, M, and S proteins produced formed virus-like particles (see FIG. 4) and provide the surface antigens, preS antigen (preS1 and preS2) and S antigen (see Example 1.1).

In still another embodiment, the present invention provides a host cell comprising the expression vector. The host cell may be preferably, but not limited to animal cells, more preferably selected from the group consisting of CHO (Chinese Hamster Ovary) cell, hepatocyte, HEK (Human Embryonic Kidney) cell, and HLF (Human Lung Fibroblast), and most preferably CHO cell.

In the preferred embodiment of the present invention, it was found that the expression vector harboring the entire HBV envelope gene according to the present invention was introduced into CHO cells to mass-produce L, M and S proteins (see Example 1.1 and FIG. 2). Accordingly, the cell line capable of coexpressing L, M and S proteins was prepared by transforming CHO cells with the expression vector according to the present invention. This cell line designated CHO DG44/L-HBsAg(J2.1)-G101, was deposited at Korea Institute of Bioscience and Biotechnology (Korean Collection for Type Cultures, Ueun-dong, Yusung-gu, Daejeon-si, Korea) on Dec. 28, 2006 under accession number KCTC 11058BP.

In still another embodiment, the present invention provides a method for preparing the HBV vaccine comprising the entire HBV surface antigen.

As described above, the cell line, which is transformed with the recombinant expression vector harboring the entire HBV envelope gene according to the present invention, coexpresses L, M and S proteins, and the coexpressed S antigens are covalently linked to each another to form particles, and the coexpressed preS antigens are located on the external surface of these particles, so as to form virus-like particles. Accordingly, the entire HBV surface antigens expressed in the cell line are purified to prepare the HBV vaccine comprising the entire HBV surface antigen according to the present invention.

Specifically, the method for preparing the HBV vaccine according to the present invention comprises the steps of 1) introducing a polynucleotide encoding HBV preS and S antigens into an expression vector;
2) transforming a host cell with the expression vector of step 1); and
3) culturing the transformed host cell of step 2) to recover a recombinant HBV entire surface antigen (preS antigen and S antigen).

The polynucleotide of step 1) comprises the entire envelope gene of Hepatitis B virus (HBV), more preferably a coding region for HBV envelope gene and an entire 3'-UTR containing polyadenylation site, and most preferably a polynucleotide having a base sequence of SEQ ID NO. 1. The expression vector of step 1) is preferably a pMSG vector (KCCM 10202). The host cell may be preferably, but not limited to, a CHO cell.

The vaccine further comprising an HBV core antigen in addition to the entire HBV surface antigen may be easily prepared by mixing the entire HBV surface antigen obtained by the preparation method of the present invention with the HBV core antigen prepared by a genetic recombination technique known in the related art. Specifically, the following steps 4) to 6) are included in the preparation method of HBV vaccine comprising steps 1) to 3) to prepare the vaccine comprising the entire HBV surface antigen and HBV core antigen:

4) introducing a polynucleotide encoding an HBV core protein into an expression vector;
5) transforming a host cell with the expression vector of step 4); and
6) culturing the transformed host cell of step 5) to recover a recombinant HBV core protein.

The expression vector of step 4) may be preferably, but not limited to, a pBluescript vector, a pGEX expression vector, a pET expression vector, a pIL20 expression vector, a pET11a expression vector, or the like. The expression vector may be introduced into prokaryotic or eukaryotic cells. Preferred examples thereof include prokaryotic cells such as *E. coli* and *B. subtilis*, and eukaryotic cells such as *Saccharomyces cerevisiae* and *Hansenula polymorpha*, but are not limited thereto, and most preferably *E. coli*.

In still another embodiment, the present invention provides a HBV vaccine composition comprising an adjuvant.

As used herein, "adjuvant" refers to a substance or supplement that cannot itself induce specific immunity, but can stimulate the immune system to increase immune responses against specific antigen. That is, vaccines containing both antigen and adjuvant induce stronger immune response than vaccines containing antigen alone.

In the present invention, aluminum compounds (aluminum sulfate, aluminum hydroxide, aluminum phosphate, etc.) may be used as adjuvants. Colloidal gold may be also used as an adjuvant. In particular, the present inventors disclosed that the colloidal gold can be used as an adjuvant to significantly enhance cell-mediated immune response (Korean Patent Application No. 10-2006-0057040). When the HBV vaccine according to the present invention is used for the treatment of chronic hepatitis B, its capability to induce a cell-mediated immune response is required. It was found that the vaccine containing colloidal gold as an adjuvant can more effectively induce a cell-mediated immune response, producing a better therapeutic vaccine (see Example 5.2 and FIG. 13).

More preferably, colloidal gold may be used with alum as an adjuvant. Alum functions to enhance humoral immunity. Thus, when both alum and colloidal gold are employed as adjuvants for the preparation of a therapeutic vaccine, both humoral and cell-mediated immunity can be effectively induced. It was found that upon using alum with colloidal gold as an adjuvant, the HBV multi-antigen vaccine according to the present invention can more effectively induce both humoral and cell-mediated immunity (see Example 6.2 and FIG. 15).

In still another embodiment, the present invention provides a therapeutic HBV vaccine. Therapeutic vaccines are suitable for the treatment of chronic infections, since they break immune tolerance and induce an immune response against the infection to recover from the infected condition. This utility was demonstrated in a transgenic animal model that produces HBV envelop antigen in the serum but no detectable amount of antibody against the HBV antigen. The HBV vaccine of the present invention induced strong cell-mediated immune response as well as humoral immune response. Accordingly, the HBV vaccine of the present invention is suitable as a therapeutic vaccine. It is preferable that the HBV vaccine of the present invention contains adjuvant. The adjuvant may be alum, colloidal gold or a combination of both The vaccine composition of the present invention may include pharmaceutically acceptable carriers, and formulated for human or veterinary use to be administered via various routes. Examples of the administration routes may include oral, intraperitoneal, intravenous, intramuscular, subcutaneous, and intradermal routes. The vaccine composition is preferably formulated into injectable preparations. The injectable preparation may be formulated using aqueous solutions such as saline solution or Ringer's solution, and non-aqueous solutions such as vegetable oil, higher fatty acid ester (e.g., ethyl oleate), and alcohols (e.g., ethanol, benzylalcohol, propyleneglycol, or glycerine). Further, the injectable preparation may contain a pharmaceutically acceptable carrier such as a stabilizer to prevent degradation (e.g., ascorbic acid, sodium bisulfite, sodium pyrosulfite, BHA, tocopherol, and EDTA), an emulsifier, a buffering agent to adjust pH, and an antimicrobial preservative (e.g., phenylmercuric nitrate, thimerosal, benzalkonium chloride, phenol, cresol, and benzylalcohol).

The composition of the present invention is administered in a pharmaceutically effective amount. The phrase "pharmaceutically effective amount" refers to an amount sufficient to exert the vaccine's effect, and further an amount that does not cause an adverse reaction, or a serious or excessive immune response. The exact concentration administered varies depending on the antigen, and can be easily determined by those skilled in the art, depending on the factors well known in the medical field including a patient's age, weight, health condition, sex, and sensitivity to drug, administration route, and administration method, and may be administered once or multiple times.

In still another embodiment, the present invention provides a method for treating chronic hepatitis B using the vaccine composition.

Hereinafter, the present invention will be described in more detail with reference to Examples. However, these Examples are for the illustrative purpose only, and the invention is not intended to be limited by these Examples.

EXAMPLES

Example 1

Preparation of HBV Vaccine

1. Preparation of Recombinant Entire Surface Antigen (preS and S Antigens; L-HBsAg).

A. Cloning

PCR was performed using a vector containing HBV genome (HBV315, Korean Biochem. J. 17:70-79, 1984) as a template to amplify a coding region of envelope gene (preS1-preS2-S) and an entire 3'-UTR containing polyadenylation site (SEQ ID NO. 1), and then introduced into an expression vector. At this time, PCR was performed using a Pfu DNA polymerase, and primers were prepared to amplify the coding region of HBsAg and the entire 3'-UTR (forward primer: 5-GGA AGATCTCAA TCT CGG GAA-3 (SEQ ID NO. 2), reverse primer: 5-GGA AGATCTCGA ATA GAA GGA AAG-3 (SEQ ID NO. 3), BglII recognition sequence is underlined). A PCR product of about 2.75 Kbp was obtained, and ligated with a pMSG vector (see Korean Patent Application No. 10-2000-0043996 and PCT/KR01/01285) which was linearized with BglII enzyme. The prepared vector (pMSG-L-HBsAg) is schematically illustrated in FIG. 1. CHO cells were transformed with the vector to give transformants, and Western blot was performed to confirm the expression of entire surface antigen (L-HBsAg, SEQ ID NO. 4), followed by screening transformants for high-level expression. The selected transformants was designated as CHO DG44/L-HBsAg(J2.1)-G101, which was deposited at Korea Institute of Bioscience and Biotechnology (Korean Collection for Type Cultures, Ueun-dong, Yusung-gu, Daejeon-si, Korea) on Dec. 28, 2006 under accession number KCTC 11058BP.

B. Establishment of Cell Line in Suspension Culture

The selected cell line ($5 \times 10^5$ cells) was inoculated in a T-175 flask. The cell line was cultured in media containing 10% serum, and the attached cells were treated with 0.25% trypsin. Then, the cells were centrifuged at 1200 rpm for 5 min to remove the residual trypsin. The single cells were resuspended in protein-free media (HyQ SFM4CH0, Hyclone), inoculated in 250 ml spinner flasks with 100 ml working volume, and cultured at 80 rpm and 37° C. The cells were inoculated at the initial concentration of $5 \times 10^5$ cells/ml. When the concentration of the cells approached $1.5 \times 10^6$ cells/ml, the cells were continuously subcultured using the same initial concentration. Finally, the cell lines adapted to suspension culture were obtained.

C. Culture

Cell inoculation was prepared by subculturing from MCB (Master Cell Bank). At this time, serum-free media (HyQ SFM4CHO, Hyclone) were used as a basic medium, and the cells were inoculated at the concentration of $5 \times 10^5$ cells/ml in 250 ml spinner flasks and cultured at 34° C. and 80 rpm. After three days, the cells were subcultured in 1 L Spinner flasks to expand the number of cells. Then, the cells were inoculated in a 7.5 L bioreactor, and cultured at pH 7.2, 34° C. and at the stirring speed of 80 rpm. After three days, citric acid and HyQ LS1000 were added, and the cells were cultured for another three days.

D. Purification

The culture media recovered from the bioreactor was centrifuged to remove cell debris and passed through a 0.45 um filter to remove impurities. The expressed HBV surface antigen was purified by an equilibrated phenyl-sepharose chromatography, DEAE-sepharose chromatography, and sepharose 4 FF chromatography. It was found that the purified entire surface antigen consists of S protein, M protein, and L protein, and consists of six kinds of recombinant proteins depending on glycosylation (FIG. 2). FIG. 2A shows the result of SDS-PAGE of the purified entire surface antigen, and FIG. 2B shows the result of Western blot of the purified entire surface antigen by using anti-S antibody (Lane 1), anti-preS1 antibody (Lane 2), and anti-preS2 antibody (Lane 3). Glycosylation of S region and preS2 region of M protein was confirmed using N-glycosidase F (FIG. 3). Further, the purified L-HBsAg was found to form virus-like particles by electromicroscopic observation (FIG. 4).

2. Preparation of Recombinant Core Antigen (HBcAg)

A. Cloning

Amino acid sequence Nos. 1 to 149, except arginine cluster at the C-terminus of core antigen, was expressed as a recombinant protein (SEQ ID NO. 5). Nucleotide sequence encoding the protein is represented by SEQ ID NO. 6. PCR was performed using a vector containing HBV genome (HBV315) as a template to amplify the corresponding region. The amplified gene was inserted into the NdeI and BamHI restriction sites of a pET11a vetor (Novagen, Gibbstown, N.J.) to prepare a pET11a-core expression vector. For the PCR amplification of the core gene, forward primer: 5-CCC CATATGGAC ATT GAC CCG TA-3 (SEQ ID NO. 7) and reverse primer: 5-CGC GGATCCAAC AAC AGT AGT TTC CGG-3 (SEQ ID NO. 8) were used. E. coli BL21 (DE3) was transformed with the pET11a-core expression vector. Its expression was confirmed, and high production clones were selected.

B. Culture of Transformed Production Strain

Optimal production conditions for the production strain were determined by using a 5 L fermentor. Media containing 2% Bacto Tryptone, 1% Yeast extract, 2% NaCl, 2% Glucose, 1.33% $KH_2PO_4$, 0.4% $(NH_4)_2HPO_4$, 0.17% Citric acid, 0.12% $MgSO_4$, 0.01% Thiamine-HCl, and 0.0371% Ampicillin was used. The strain was cultured at 37° C. for 11 hours, and then IPTG (Isopropyl-β-D-thiogalactopyranoside) was added in an amount of 0.05 mM/g cell. Then, the cells were subjected to induction by IPTG for 18 hours, and harvested.

C. Purification of Recombinant Protein

The cells were harvested, and washed three times with a lysis buffer (50 mM Tris-Cl pH7.6, 150 mM NaCl, 5 mM EDTA, 10 mM 2-mercaptoethanol, 0.2 mM PMSF). Then, the lysis buffer was added, and the cells were disrupted by sonication. The supernatant was collected by centrifugation, and incubated at 65° C. for 30 min. Then, the supernatant was collected by centrifugation, and 30% ammonium sulfate was added to precipitate core antigens. After centrifugation, the precipitate was dissolved in 50 mM Tris-Cl (pH 7.6), and passed through a butyl sepharose column to isolate the pure core antigens.

The purified recombinant core antigens were found to multimerize in a particle form (FIG. 5). FIG. 5A shows the result of SDS-PAGE of the purified recombinant core antigen, and FIG. 5B shows the result of Western blot of the purified recombinant core antigen. Multimerization was confirmed under reduced and non-reduced-conditions. Further, the purified recombinant core antigens were found to form particles by electromicroscopic observation (FIG. 6).

It was found that the purified recombinant core antigens formed virus-like particles, and were highly immunogenic and induced strong cell-mediated immunity (in the following Example).

Example 2

Comparison of Immunogenicity of Recombinant Entire Surface Antigen (L-HBcAg)

In order to confirm whether the recombinant entire surface antigen (L-HBsAg) of the present invention is highly immunogenic and induces strong immune responses, animal test was performed to compare with known second-generation HBV vaccines.

1. Comparison of Immunogenicity

A. Test Vaccine

The entire surface antigen (L-HBsAg) was prepared and purified according to Example 1 and was adsorbed onto alum to prepare the test vaccine. As a control group, a recombinant S antigen produced in *Hansenula polymorpha* (Hepavax-Gene, Green Cross Co. Gyeonggi-do Korea) and recombinant S antigen produced in CHO cell, which contains no preS antigen, (Recombinant Hepatitis B Vaccine, Hualton, China) were used. 0.5 μg of each antigen per dose was used.

B. Immunization Group and Immunization Condition
Immunization Groups

Group 1: recombinant S antigen produced in *Hansenula polymorpha* (Hepavax-Gene, Green Cross Co., Gyeonggi-do Korea)

Group 2: recombinant S antigen produced in CHO cell (Recombinant Hepatitis B Vaccine, Hualton, China)

Group 3: recombinant L-HBsAg antigen produced in CHO cell, prepared and purified according to Example 1

Each test vaccine was administered by intramuscular injection three times at two-week intervals into 6 week old female C57BL/6 mice.

C. Analysis Method of Immune Response

Antibody titer was determined as international unit (mIU/ml) using a Diasorin kit to analyze humoral immune responses induced by each test vaccine.

D. Results

It was found that the recombinant L-HBsAg according to the present invention induced stronger humoral immune response to exhibit higher antibody titer, as compared to the recombinant S antigens used in the known vaccines (FIG. 7). That is, the recombinant L-HBsAg was found to have higher immunogenicity than the known antigens. Further, the recombinant L-HBsAg was found to induce a faster immune response, as compared to the S antigen produced in *Hansenula polymorpha*.

2. Comparison of ED50 Values

A. Test Vaccine

The immunogenicity of the recombinant L-HBsAg antigen, prepared and purified according to Example 1, was compared by ED50 (Effective Dose), which is the minimum amount of antigen required for sero-conversion in 50% of mice. The entire surface antigen (L-HBsAg) prepared and purified according to Example 1-1 was adsorbed onto alum to prepare a test vaccine. As a control group, a recombinant S antigen produced in yeast (Recombinant Hepatitis B Vaccine, Kangtai, China) and recombinant S antigen produced in CHO cell, which contains no preS antigen, (Recombinant Hepatitis B Vaccine, Hualton, China) were used. Each vaccine was diluted to prepare vaccines containing 0.156 μg, 0.312 μg, 0.625 μg, 1.25 μg, 2.5 μg, and 5 μg of each antigen per dose.

B. Immunization Group and Immunization Condition

Each group of 6 week-old female C57BL/6 mice was divided into six subgroups consisting of 10 mice, and each subgroup was immunized with each diluted vaccine.

Group 1: recombinant S antigen produced in yeast (Recombinant Hepatitis B Vaccine, Kangtai, China) (Group 1-1: 0.156 μg administration, Group 1-2: 0.312 μg administration, Group 1-3: 0.625 μg administration, Group 1-4: 1.25 μg administration, Group 1-5: 2.5 μg administration, Group 1-6: 5 μg administration)

Group 2: recombinant S antigen produced in CHO cell, used in Example 2 as a control group (Recombinant Hepatitis B Vaccine, Hualton, China) (Group 2-1: 0.156 administration, Group 2-2: 0.312 μg administration, Group 2-3: 0.625 μg administration, Group 2-4: 1.25 μg administration, Group 2-5: 2.5 μg administration, Group 2-6: 5 μg administration)

Group 3: recombinant L-HBsAg antigen produced in CHO cell, prepared and purified according to Example 1 (Group 3-1: 0.156 μg administration, Group 3-2: 0.312 μg administration, Group 3-3: 0.625 μg administration, Group 3-4: 1.25 μg administration, Group 3-5: 2.5 μg administration, Group 3-6: 5 μg administration)

Each test vaccine was administered by intraperitoneal injection once.

C. Analysis Method of Immune Response

Antibody titer was determined in international units (mIU/ml) using a Diasorin kit to analyze humoral immune responses induced in each individual. Antibody titer of 10 mIU/ml was defined as sero-conversion. In each group, the amount of antigen required for sero-conversion in 50% of immunized mice (ED50) was determined.

3. Results

The vaccine containing the recombinant L-HBsAg antigen prepared and purified according to Example 1 has the lowest ED50 value, compared to the known vaccines. That is, the recombinant L-HBsAg according to the present invention was found to effectively induce a humoral immune response, compared to the known antigens (FIG. 8).

Example 3

Comparison of Immune Response by HBV Vaccine

1. Conditions for Immunization Experiment and Analysis Method

A. Immunization of Mice

In order to confirm the efficacy of HBV vaccine prepared according to the present invention, 6 week-old female C57BL/6 mice were immunized with the vaccine containing only the entire HBV surface antigen (hereinafter, referred to as 'single antigen vaccine') or the vaccine containing both of the entire HBV surface antigen and core antigen (hereinafter, referred to as 'multi-antigen vaccine') to analyze the induced immune responses.

B. Test Vaccine

Each of the recombinant core antigen and entire surface antigen prepared and purified in Example 1 was adsorbed onto alum to prepare single antigen vaccines. The recombinant core antigen and entire surface antigen adsorbed onto alum were mixed with each other to prepare a multi-antigen vaccine. 0.5 μg of each antigen per dose was used.

C. Immunization Group and Immunization Condition
Immunization Groups

Group 1: negative control immunized with PBS (Phosphate buffered saline)

Group 2: recombinant entire surface antigen adsorbed onto alum

Group 3: recombinant core antigen adsorbed onto alum

Group 4: recombinant entire surface antigen and recombinant core antigen adsorbed onto alum (multi-antigen vaccine). Each test vaccine was administered by intramuscular injection three times at two-week intervals.

D. Analysis Method of Immune Response

1) Analysis of Humoral Immune Response

Pre-immune sera and sera at 2 weeks after immunization were separated, and the antibodies produced in the sera were analyzed by ELISA to determine antibody titer. First, 96 well-microtiter plates were coated with each purified antigen at a concentration of 100 ng/well, and blocked with Bovine Serum Albumin (1%) for 1 hour. The microtiter plates were washed. The serially diluted sera were added to each well, and incubated at 37° C. for 2 hours. Then, anti-mouse IgG-HRP was added as a secondary antibody, and incubated for 1 hour under the same condition. After washing, a developing agent was added, and incubated at room temperature for 20 minutes. Then, OD value was measured at 450 nm using an ELISA reader. The antibody titer was defined as the inverse of the dilution fold at which the OD value was threefold greater than the negative control.

2) Analysis of Cell-Mediated Immune Response.

After the last immunization, spleens were taken out from all of the mice, and total splenocytes were isolated and cultured. The γ-interferon-secreting splenocytes were analyzed by an ELISPOT assay to confirm the cell-mediated immune response.

At 2 weeks after the tertiary immunization, the spleens separated from each mouse were put in a cell strainer, and crushed. Then, the red blood cells were completely removed using an RBC lysis buffer, and splenocytes were isolated. The isolated splenocytes were cultured in complete media (1× glutamine and 1× antibiotics in RPMI1640 medium). To observe the immune responses being specific to each antigen, the core antigen and entire surface antigen were added to the culture media at a concentration of 1 μg/ml to stimulate antigen-specific immune cells. Then, the number of γ-IFN-secreting cells (indication of cell-mediated immune response) was analyzed by the ELISPOT assay (BD Biosciences).

2. Effect on Humoral Immune Response.

In the group administered with the multi-antigen vaccine containing both of the recombinant entire surface antigen (L-HBsAg) and recombinant core antigen, the anti-HBs antibodies were induced faster, compared to the single antigen vaccine containing only the recombinant entire surface antigen (L-HBsAg) (FIG. 9). In the case of mixing with the recombinant core antigen, an enhanced humoral immune response was observed. However, after the last immunization, the single antigen vaccine and multi-antigen vaccine exhibited same antibody titers.

3. Effect on Cell-Mediated Immune Response

In the group administered with the multi-antigen vaccine containing both the recombinant entire surface antigen (L-HBsAg) and recombinant core antigen, a higher cell-mediated immune response was observed, compared to the single antigen vaccine containing only the recombinant entire surface antigen (L-HBsAg) or the single antigen vaccine containing only the recombinant core antigen (FIG. 10). In the case of mixing with the recombinant core antigen, the cell-mediated immune response can be more effectively induced. Accordingly, the multi-antigen vaccine is preferably used as a therapeutic vaccine for the induction of cell-mediated immune response.

Example 4

Preparation of Colloidal Gold Adjuvant

1. Preparation of Colloidal Gold

Colloidal gold was prepared by a method based on the sodium citrate procedure, which was developed by Frens (Frens G., Nature Phys. Sci. 241:20, 1973). 0.2 g of gold chloride (HAuCl$_4$3H$_2$O) was dissolved in 10 ml of distilled water to prepare a 2% gold stock solution. 100 ml of distilled water was heated under stirring, and 1 ml of the 2% gold stock solution was added to a final concentration of 0.02% and maintained under heating and stirring for about 5 minutes. 10% sodium citrate solution was added to a final concentration of 0.032 to 0.036%, and maintained under heating and stirring for 5 to 10 minutes. At this time, the color of the solution was initially gray, gradually changed to violet, and after 1 to 3 minutes, changed to red. The solution was put in a water bath, and cooled. Then, OD$_{540}$ and OD$_{600}$ were measured. The number or concentration of gold particles was measured by reading OD$_{540}$ value, which was 2 to 4. The particle size or quality was measured by reading OD$_{600}$ value, which was 0.55 to 0.75 values. The particle size of the prepared colloidal gold was about 10 to 40 nm.

2. Preparation of Colloidal Gold Conjugate 100 mM sodium carbonate monohydrate (or other buffer) was added to the prepared colloidal gold solution, and the pH of the solution was titrated to 7.5. Then, while stirring the colloidal gold solution, 20 μg of bovine serum albumin (BSA) or 10 μg of preS antigen per 1 ml of the solution (containing 200 μg of colloidal gold) was added, and continuously stirred at room temperature for 15 minutes. After centrifugation, the supernatant was removed, and the precipitate was washed three times with a sterilized PBS buffer (Phosphate Buffered Saline) to remove unbound BSA or preS antigen. Then, the precipitate was resuspended in the PBS buffer, and stored at 4° C. An electron microscopic photograph of colloidal gold conjugate coated with preS protein is shown in FIG. 1 (JEM1010, 67.0 k). The amount of proteins in the supernatant, which was obtained by centrifugation after the BSA or preS antigen adsorption, was measured to quantify protein adsorption.

Example 5

Effect of Colloidal Gold Adjuvant on Induction of Immune Response

1. Conditions for Immunization Experiment and Analysis Method

A. Test Vaccine

To confirm the efficacy of colloidal gold conjugate as an adjuvant, the immune response induced in immunized mice was analyzed. The purified recombinant core antigen and entire surface antigen were adsorbed onto alum to prepare a test vaccine. 0.5 μg of each antigen per dose was used. Further, 0.5 μg of free antigen, not adsorbed onto alum, was mixed with 200 μg of colloidal gold conjugate.

B. Immunization Group and Immunization Condition

Immunization Group

Group 1: negative control immunized with PBS (Phosphate buffered saline)

Group 2: immunized with recombinant entire surface antigen and core antigen adsorbed onto alum Group 3: immunized with the mixture of colloidal gold conjugates, and recombinant entire surface antigen and core antigen which were not adsorbed onto alum Each test vaccine was administered by intramuscular injection twice at two-week intervals into 6 week-old female C57BL/6 mice.

C. Analysis Method of Immune Response

1) Analysis of Humoral Immune Response

Humoral immune response was analyzed by ELISA, as described in Example 3 above.

2) Analysis of Cell-Mediated Immune Response

Within 2 weeks after the secondary immunization, spleens were removed from all of the mice, and total splenocytes were isolated and cultured to analyze the cell-mediated immune response. The spleens from each mouse were put in a cell strainer, and crushed. Then, the red blood cells were completely removed using an RBC lysis buffer, and splenocytes were isolated. The isolated splenocytes were cultured in complete media (1× glutamine and 1× antibiotics in RPMI1640 medium). To observe the immune responses being specific to each antigen, the core antigen and entire surface antigen was added to the culture media at a concentration of 1 μg/ml to stimulate antigen-specific immune cells. Then, the cytokine (γ-interferon as an indication of cell-mediated immune response) secreted from the cells were analyzed by an ELISA kit (BD Biosciences, Franklin Lakes, N.J.).

2. Efficacy of Colloidal Gold Conjugate as Adjuvant

A. Effect on Humoral Immune Response

In Group 2 and 3 administered with vaccine antigens, anti-HBs antibody and anti-HBc antibody being specific to each antigen were induced, compared to the negative control group (Group 1). However, higher antibody formation was found in the case of using alum as an adjuvant (Group 2) than in the case of using colloidal gold conjugate as an adjuvant (Group 3) (FIG. 12). Alum, as previously known, is an adjuvant capable of inducing strong humoral immune response. The colloidal gold conjugate used in the present invention was also found to induce humoral immune response. However, to compare two adjuvants as an adjuvant for therapeutic vaccine, the cell-mediated immune responses induced by two adjuvants were compared to each other.

B. Effect on Cell-Mediated Immune Response

To confirm whether cell-mediated immune response was induced by the colloidal gold conjugate, splenocytes after secondary immunization were removed from each mouse, and the production of γ-interferon being specific to the core antigen or surface antigen was analyzed by ELISA. In the case of using alum as an adjuvant (Group 2), the production of antigen-specific γ-interferon was increased 2.5 times over the non-immunized control group. In the case of using the colloidal gold conjugate as an adjuvant, the production of antigen-specific γ-interferon was increased much more than the non-immunized control group (FIG. 13), in particular, the surface antigen-specific cell-mediated immune response was increased 4 times over using alum. That is, when the colloidal gold conjugate was used as an adjuvant, the cell-mediated immune response against hepatitis B virus antigen was effectively induced to increase the production of γ-interferon for virus removal. Accordingly, the colloidal gold conjugate can induce strong cell-mediated immune response, thereby making it a good adjuvant in the development of an effective therapeutic vaccine.

Example 6

Optimization of Therapeutic Vaccine

1. Conditions for Immunization Experiment and Method of Analysis

A. Test Vaccine

To maximize both humoral and cell-mediated immune responses, the optimal compositions of therapeutic vaccine were compared. The purified recombinant core antigen and entire surface antigen were adsorbed onto alum. 0.5 µg of each antigen per dose was used. Further, 0.5 µg of each antigen adsorbed onto alum was mixed with 200 µg of the colloidal gold conjugate coated with BSA, and the immunization was performed.

B. Immunization Group and Immunization Condition

Immunization Group

Group 1: negative control immunized with PBS.

Group 2: immunized with the recombinant entire surface antigen and core antigen adsorbed onto alum.

Group 3: immunized with the mixture of colloidal gold conjugates, and recombinant entire surface antigen and core antigen which were adsorbed onto alum Each test vaccine was administered by intramuscular injection twice at two-week intervals in 6 week-old female C57BL/6 mice.

C. Analysis Method of Immune Response

Humoral and cell-mediated immune responses induced by the test vaccines were analyzed in the same manners as described in Examples 3 and 5 above.

2. Analysis of Induced Immune Responses

A. Effect on Humoral Immune Response

Antigen-specific antibody formation was induced in the Groups administered with vaccine antigens (Groups 2 and 3), compared to the negative control (Group 1). There was no significant difference in the antibody titers between Group 2 (immunized with the antigens adsorbed onto alum) and Group 3 (immunized with the mixture of the colloidal gold conjugate and antigens adsorbed onto alum) (FIG. 14). As a result, alum and colloidal gold conjugates were mixed to use as an adjuvant, thereby enhancing the humoral immune response.

B. Effect on Cell-Mediated Immune Response

To confirm whether cell-mediated immune response was induced by the colloidal gold conjugate, splenocytes were removed from mice after the secondary immunization and the production of γ-interferon was analyzed by ELISA.

In Group 2, immunized with the vaccine antigens adsorbed onto alum, the production of antigen-specific γ-interferon was doubled when compared to the negative control group. In Group 3 immunized with the vaccine antigens and colloidal gold conjugate, the production of core antigen-specific interferon-g was increased by 2.5 times and the production of surface antigen-specific interferon-g was increased by 4.5 times (FIG. 15) over the control group. Therefore, it has been confirmed again that alum is an adjuvant capable of inducing strong humoral immune response and the colloidal gold conjugate is an adjuvant capable of inducing a strong cell-mediated immune response, as shown in Example 4. Consequently, the immunization is performed using the mixture of vaccine antigens adsorbed onto alum and the colloidal gold conjugate to optimize both humoral and cell-mediated immune responses.

Example 7

Confirmation of Vaccine Efficacy in Transgenic Mice

1. Conditions for Immunization Experiment and Method of Analysis

A. Experimental Animal the efficacy of therapeutic vaccine composition established in normal mouse was analyzed in transgenic mouse (HBsAg/HLA-A2). Six week-old female HBsAg/HLA-A2 transgenic mice were used (Loirat D. et al., HBsAg/HLA-A2 transgenic mice: a model for T cell tolerance to hepatitis B surface antigen in chronic hepatitis B virus infection International Immunology 15: 1125-1136, 2003). The mouse model continuously expresses HBV surface antigen (HBsAg), and secrets virus-like particles consisting of surface antigens into blood. Further, the mouse model recognizes the HBV surface antigen gene as a self gene, and does not induce the immune response against the gene, exhibiting immune tolerance. Basically, this is a mouse model for HBV chronic carriers, in which the immune response against HBV antigen is too weak to remove the virus antigen and the condition of chronic infection is maintained.

B. Vaccine Antigen and Adjuvant

The purified recombinant core antigen and entire recombinant surface antigen were adsorbed onto alum to use as a vaccine antigen. The colloidal-gold conjugate coated with BSA was used as an adjuvant for therapeutic vaccine.

C. Immunization Group and Immunization Condition
Immunization Group

Group 1: negative control immunized with PBS (Phosphate buffered saline).

Group 2: immunized with the recombinant entire surface antigen and core antigen adsorbed onto alum.

Group 3: immunized with the mixture of colloidal gold conjugates, and recombinant entire surface antigen and core antigen which were adsorbed onto alum Each test vaccine was administered by intramuscular injection three times at two-week intervals.

D. Analysis of Virus-Like Particle in Serum

Pre-immune sera and sera after the tertiary immunization were collected, and the amount of virus-like particles consisting of the surface antigen (HBsAg) in the serum was analyzed using a Genedia HBsAg ELISA kit 3.0 (Green Cross Co., Gyeonggi-do Korea).

E. Analysis of Humoral Immune Response

Pre-immune sera and sera after the tertiary immunization were collected, and the antigen-specific antibody formation was analyzed in the same manner as described in Example 4 above. Further, the subtype of induced antibody was determined to measure the ratio of IgG2a and IgG1.

F. Analysis of Cell-Mediated Immune Response

Splenocytes were separated and cultured by the method as described in Example 4 above, and the induction of γ-interferon as an indication of cell-mediated immune response was analyzed by ELISA and ELISPOT assay.

G. Analysis of Interferon-G and Surface Antigen Gene Expression in Liver

Total RNA was extracted from the mouse liver, and the gene expression was analyzed by a RT-PCR method. Total RNA was isolated using an RNeasy Mini kit (Qiagen, Valencia, Calif.) and the expression of surface antigen gene (SEQ ID NOs. 9 and 10) and γ-interferon gene (SEQ ID NOs. 11 and 12) were analyzed using the following primers and a one-step RT-PCR kit (Qiagen, Valencia, Calif.). The expression of β-actin gene (SEQ ID NOs. 13 and 14) was used as a negative control.

```
                                              (SEQ ID NO. 9)
S-(F)       5'-ATG GAG AGC ACA ACA TCA GG-3'

(SEQ ID NO. 10)
S-(R)       5'-TTA AAT GTA TAC CCT AAG-3'

(SEQ ID NO. 11)
INF-γ(F)    5'-AGC GGC TGA CTG AAC TCA GAT TGT AG-3'

(SEQ ID NO. 12)
INF-γ(R)    5'-GTC ACA GTT TTC AGC TGT ATA GGG-3'

(SEQ ID NO. 13)
β-actin(F)  5'-TCC TGT GGC ATC CAT GAA AC-3'

(SEQ ID NO. 14)
β-actin(R)  5'-CTT CGT GAA CGC CAC GTG C-3'
```

2. Efficacy of Colloidal Gold Conjugate as Adjuvant for Therapeutic Vaccine

A. Breakage of Immune Tolerance

The transgenic mouse model recognizes the HBV surface antigen as a self antigen and does not induce an immune response against the antigen, exhibiting immune tolerance. However, when the mouse model was administered with the therapeutic vaccine, the immune tolerance to the surface antigen was broken and both humoral and cell-mediated immune responses were induced.

1) Induction of Humoral Immune Response

The antibody titer against the surface antigen was determined using the pre-immune sera and sera after the tertiary immunization. Even though the high concentration of antigen in the blood was maintained in the negative control (Group 1), no antibody against the surface antigen was detected. However, in the group administered with the vaccine antigen (Groups 2 and 3), immune tolerance to the surface antigen was broken, and the antibody against the surface antigen was produced. In the case of using the colloidal gold conjugate coated with BSA as an adjuvant (Group 3), the production of the induced antibody was slightly lower, compared to the group administered with the vaccine antigen adsorbed onto alum (Group 2) (FIG. 16). However, the ratio of IgG2a to IgG1 was found to be higher in Group 3 using the colloidal gold conjugate as an adjuvant than Group 2 using alum only (FIG. 17). Accordingly, it can be seen that the colloidal gold conjugate as an adjuvant skewed the immune response toward Th1 response.

2) Induction of Cell-Mediated Immune Response

It has been known that strong cell-mediated immune response is essential for virus removal. Therefore, to confirm whether the therapeutic vaccine breaks immune tolerance and induces the surface antigen-specific cell-mediated immune response, splenocytes were removed from mice after immunization and the production of γ-interferon as an indication of the cell-mediated immune response by ELISPOT and ELISA were compared. In the experiment using the transgenic mice, a higher cell-mediated immune response was also induced in Group 3 using the colloidal gold conjugate as an adjuvant (A and B in FIG. 18), which is similar to the results in Example 5 above.

B. Reduction of Virus-Like Particles Consisting of Surface Antigen (HBsAg) in Blood The pre-immune sera and sera after the tertiary immunization were collected to analyze the amount of virus-like particles consisting of the surface antigen (HBsAg) in blood. As previously reported, the amount of virus-like particles in blood was naturally reduced by about 40% in the negative control. However, the amounts of virus-like particles in blood were significantly reduced in Groups immunized with the therapeutic vaccine. Further, after the tertiary immunization, the least amount of virus-like particles were detected in Group 3 immunized with the mixture of the vaccine antigens and colloidal sold conjugate, as compared to Group 2 immunized with only the vaccine antigens adsorbed onto alum (FIG. 19). In Group 2 immunized with only the vaccine antigens adsorbed onto alum, the amount of antigen was found to be temporarily reduced, however, a cell-mediated immune response was not induced. Therefore, it was not thought to completely remove virus.

C. Reduction of Virus Gene Expression in Liver by Cell-Mediated Immune Response

To remove virus from the infected hepatocytes, immune cells secreting γ-interferon and having cytolytic activity have to migrate to the liver to suppress the transcription of viral gene and directly destroy the infected cells. Therefore, to confirm whether the antigen-specific cell-mediated immune response is actually induced in the liver of transgenic mice, total RNA was extracted from mouse liver, and the expression of the γ-interferon was analyzed by RT-PCR method. The expression of γ-interferon was found to be low in the control group (Group 1) and Group 2, whereas the expression of the γ-interferon was found to be 3 to 4 times higher in Group 3 (FIG. 20). Further, to confirm whether the produced γ-interferon suppresses the expression of viral gene, that is, HBV surface antigen gene in hepatocytes, the same method as described above was performed to compare the expression of surface antigen gene. High expression level of surface antigen was found to be maintained in the control group (Group 1) and Group 2 immunized with only the antigens adsorbed onto alum. In contrast, the expression of surface antigen was found to be markedly decreased in Group 3 (FIG. 20).

Consequently, it can be seen that the therapeutic vaccine of the present invention breaks immune tolerance to hepatitis B virus antigen, and induces both humoral and cell mediated immune responses. In particular, it was found that the colloidal gold as an adjuvant induced strong cell-mediated immune response to suppress the expression of viral gene in hepatocytes and remove virus-like particles from the blood. Accordingly, these experiments demonstrated that the therapeutic vaccine containing colloidal gold as an adjuvant of the present invention breaks immune tolerance to induce antigen-specific immune responses, thereby making it well suited for resolving chronic infection.

Example 8

Confirmation of Vaccine Efficacy in Transgenic Mice

1. Conditions for Immunization Experiment and Method of Analysis

Colloidal gold conjugate coated with a portion of HBV surface antigen, preS protein was used as an adjuvant for therapeutic vaccine. Experimental animals, immunization groups, and analysis methods were the same as described in Example 7 above.

2. Efficacy of Colloidal Gold-Conjugate Coated with preS as Adjuvant for Therapeutic Vaccine A. Breakage of Immune Tolerance In the case of using the colloidal gold conjugate coated with preS as an adjuvant for therapeutic vaccine, the immune tolerance was broken and both humoral and cell-mediated immune responses were induced, as shown in Example 6 (using colloidal gold conjugate coated with BSA).

1) Induction of Humoral Immune Response

The antibody titer against the surface antigen was determined using the pre-immune sera and sera after the tertiary immunization. Even though the high concentration of antigen in the blood was maintained in the negative control (Group 1), no antibody against the surface antigen was detected. However, in the group administered with the vaccine antigen (Groups 2 and 3), immune tolerance to the surface antigen was broken, and the antibody against the surface antigen was produced. In the case of using the colloidal gold conjugate coated with BSA as an adjuvant (Group 3), the production of the induced antibody was slightly lower, compared to the group administered with the vaccine antigen adsorbed onto alum (Group 2) (FIG. 21). However, the ratio of IgG2a to IgG1 was found to be higher in Group 3 using the colloidal gold conjugate as an adjuvant than Group 2 using alum only (FIG. 22). Accordingly, it can be seen that the colloidal gold conjugate as an adjuvant skewed the immune response toward Th1 response.

2) Induction of Cell-Mediated Immune Response

It has been known that strong cell-mediated immune response is essential for virus removal. Therefore, to confirm whether the therapeutic vaccine breaks immune tolerance and induces the surface antigen-specific cell-mediated immune response, splenocytes were removed from mice after immunization and the production of γ-interferon as an indication of the cell-mediated immune response by ELISPOT and ELISA were compared. In the experiment using transgenic mice, higher cell-mediated immune response was also induced in Group 3 using the colloidal gold conjugate as an adjuvant (A and B in FIG. 23), which is similar to the results in Example 5 above.

B. Reduction of Virus-Like Particles Consisting of Surface Antigen (HBsAg) in Blood The pre-immune sera and sera after the tertiary immunization were collected to analyze the amount of virus-like particles consisting of the surface antigen (HBsAg) in blood. As previously reported, the amount of virus-like particle in blood was naturally reduced in the negative control. However, the amounts of virus-like particles in blood were significantly reduced in Groups immunized with the therapeutic vaccine. Further, after the tertiary immunization, the least amount of virus-like particles were detected in Group 3 immunized with the mixture of the vaccine antigens and colloidal gold conjugate, as compared to Group 2 immunized with only the vaccine antigens adsorbed onto alum (FIG. 24). In Group 2 immunized with only the vaccine antigens adsorbed onto alum, the amount of antigen was found to be temporarily reduced, however, a cell-mediated immune response was not induced. Therefore, it was not thought to completely remove virus.

EFFECTS OF THE INVENTION

As described above, the present invention provides an HBV vaccine comprising an entire hepatitis B surface antigen consisting of preS1, preS2 and S antigens (L-HBsAg), and a multi-HBV antigen vaccine comprising the entire surface antigen and a recombinant core antigen. The vaccine further comprises colloidal gold as an adjuvant to induce strong cell-mediated immune response, thereby being used as a therapeutic vaccine for Hepatitis B virus.

What is claimed is:

1. An HBV vaccine particle comprising an entire recombinant HBV surface antigen (L-HBsAg), wherein the entire recombinant HBV surface antigen consists of L surface protein, M surface protein and S surface protein co-expressed by a recombinant expression vector comprising a base sequence of SEQ ID NO:1, wherein the L surface protein comprises a preS1 antigen, a preS2 antigen and an S antigen, the M-surface protein comprises a preS2 antigen and an S antigen and the S protein comprises an S antigen, and wherein the preS1 and preS2 antigens are located on the external surface of the particle formed by bonds between S antigens.

2. The HBV vaccine particle according to claim 1, further comprising a recombinant HBV core antigen.

3. The HBV vaccine particle according to claim 2, wherein the recombinant HBV core antigen is obtained from a recombinant expression vector comprising a nucleotide base sequence of SEQ ID NO:6.

4. The HBV vaccine particle according to claim 2, wherein the recombinant HBV core antigen is obtained from *E. coli* transformed with a recombinant expression vector comprising a nucleotide base sequence of SEQ ID NO:6.

5. An HBV vaccine comprising the HBV vaccine particle according to claim 1 and an adjuvant.

6. The HBV vaccine according to claim 5, wherein the adjuvant is alum or colloidal gold.

7. The HBV vaccine according to claim 5, wherein the adjuvant contains both alum and colloidal gold.

8. A recombinant expression vector that coexpresses HBV L surface protein, M surface protein and S surface protein, comprising a coding region for entire HBV envelope gene and an entire 3'-UTR nucleotide containing polyadenylation site, wherein the coding region for entire HBV envelope gene comprises a base sequence of SEQ ID NO:1.

9. The recombinant expression vector according to claim 8, obtained by inserting a coding region for entire HBV envelope gene and an entire 3'-UTR nucleotide containing polyadenylation site into a pSGM vector (accession number: KCCM 10202).

10. A cell transformed with the recombinant expression vector according to claim 8.

11. The cell according to claim 10, wherein the cell is identified by accession number KCTC 11058BP.

12. A method for preparing an HBV vaccine particle, comprising the steps of: 1) introducing a coding region for entire HBV envelope gene that when transcribed and translated produces the entire HBV surface antigen protein (L-HBsAg) and an entire 3'-UTR nucleotide containing polyadenylation site, into a pSGM vector (accession number: KCCM 10202) forming an HBV envelope protein expression vector; 2) transforming a cell with the HBV envelope protein expression vector to form a transformed cell; and 3) culturing the transformed cell to recover the HBV surface antigen protein (L-HBsAg), wherein the entire HBV envelope gene comprises a base sequence of SEQ ID NO:1.

13. The method according to claim 12, wherein the cell is an animal cell.

14. The method according to claim 13, wherein the animal cell is CHO cell.

15. The method according to claim 12, wherein the transformed cell is a transformant identified by accession number KCTC 11058BP.

* * * * *